United States Patent [19]

Skeels et al.

[11] Patent Number: 4,892,720

[45] Date of Patent: Jan. 9, 1990

[54] SUBSTITUTED ALUMINOSILICATE COMPOSITIONS AND PROCESS FOR PREPARING SAME

[75] Inventors: Gary W. Skeels, Brewster; Richard Ramos, Bronx, both of N.Y.

[73] Assignee: UOP, Des Plaines, Ill.

[21] Appl. No.: 604,179

[22] Filed: Apr. 26, 1984

[51] Int. Cl.⁴ .................. C01B 33/28; C01G 23/04; C01G 49/02

[52] U.S. Cl. .................................... 423/328; 423/118; 423/594; 423/598; 502/85

[58] Field of Search ............... 423/326, 328, 118, 594, 423/598; 502/60, 66, 71, 74, 77, 78, 79, 85

[56] References Cited

U.S. PATENT DOCUMENTS

| | | | |
|---|---|---|---|
| 1,759,919 | 5/1930 | Singer | 423/328 M |
| 3,373,109 | 3/1968 | Frilette et al. | 423/328 M |
| 3,403,975 | 10/1968 | Frilette et al. | 423/328 M |
| 3,702,886 | 11/1972 | Argauer et al. | 423/328 |
| 3,709,979 | 1/1973 | Chu | 423/328 |
| 3,941,871 | 3/1976 | Dwyer et al. | 423/331 |
| 4,208,305 | 6/1980 | Kouwenhoven et al. | 423/328 |
| 4,371,628 | 2/1983 | Nanne et al. | 423/328 |
| 4,372,930 | 2/1983 | Short et al. | 423/328 M |
| 4,410,501 | 10/1983 | Taramasso et al. | 423/326 |
| 4,503,023 | 3/1985 | Breck et al. | 423/328 |

FOREIGN PATENT DOCUMENTS

| | | | |
|---|---|---|---|
| 89401 | 1/1989 | Australia . | |
| 0077522 | 4/1983 | European Pat. Off. . | |
| 0132550 | 2/1985 | European Pat. Off. | 423/328 M |
| 2831611 | 2/1980 | Fed. Rep. of Germany | 423/326 |
| 3141283 | 6/1981 | Fed. Rep. of Germany . | |
| 3801900 | 3/1983 | Japan | 423/328 M |
| 1092141 | 5/1984 | U.S.S.R. | 423/328 M |
| 2024790 | 1/1980 | United Kingdom | 423/326 |

OTHER PUBLICATIONS

F. Albert Cotton, "*Advanced Inorganic Chemistry*", 2nd edition (John Wiley & Sons, New York), Chapter 29, pp. 799–808 (1976).

D. H. Olson et al., "Chemical and Physical Properties of the ZSM-5 Substitutional Series", *J. of Catalysis*, 61, 390–396 (1986).

Charles F. Baes et al., *The Hydrolysis of Cations* (John Wiley & Sons, New York, 1976), pp. 112–123, 226–237.

Charles F. Baes et al., "The Thermodynamics of Cation Hydrolysis", *Am. J. of Science*, vol. 281, Summer 1981, pp. 935–962.

G. Calis and P. Frenken, "Synthesis and Spectroscopic Studies of $Fe^{3+}$ Substituted ZSM-5 Zeolite", *Zeolites*, vol. 7, Jul. 1987, pp. 319–326.

Philippe Bodart et al., "Aluminum Siting in Mordenite and Dealumination Mechanism", *J. of Physical Chemistry*, vol. 90, No. 21, pp. 5183–5190 (1986).

Tielen et al., Proceedings of the International Symposium on Zeolite Catalysis, Siofok, Hungary, May 13, 1985.

Perego et al., "Titanium–Silicalite: a Novel Derivative in the Pentasil Family", in New Developments in Zeolite Science and Technology, Proceedings of the 7th International Zeolite Conference, Tokyo, Aug. 17–22, 1986 (Y. Murakami, A. Iijima, J. W. Ward, eds.). Elsevier, 1986.

*Primary Examiner*—John Doll
*Assistant Examiner*—R. Bruce Breneman
*Attorney, Agent, or Firm*—Thomas K. McBride; Eugene I. Snyder; Frank S. Molinaro

[57] ABSTRACT

Molecular sieve compositions are prepared by extracting aluminum and substituting titanium and/or iron for extracted aluminum to give molecular sieve products containing framework titanium and/or iron atoms. The process of preparing the titanium and/or iron-containing molecular sieves involves contacting a starting zeolite with a solution or slurry of a fluoro salt of titanium and/or iron under effective process conditions to provide for aluminum extraction and substitution of titanium and/or iron.

14 Claims, No Drawings

SPOT PROBE AT POINT A OF FIG. 2

SPOT PROBE AT POINT J OF FIG. 3

SUBSTITUTED ALUMINOSILICATE COMPOSITIONS AND PROCESS FOR PREPARING SAME

FIELD OF THE INVENTION

The instant invention relates to novel zeolite compositions the method for their preparation and to processes employing them. More particularly it relates to zeolite compositions topologically related to prior known zeolites but which are characterized as containing framework atoms of iron and/or titanium, and preferably having a very low content of defect sites in the structure, as hereinafter disclosed. In general the preparative process involves contacting the starting zeolite under controlled conditions with an aqueous solution of a fluoro salt of titanium and/or iron, preferably a fluoro salt which does not form insoluble salts with aluminum.

BACKGROUND OF THE INVENTION

The crystal structures of naturally occurring and as-synthesized zeolitic aluminiosilicates are composed of $AlO_4^-$ and $SiO_4$ tetrahedra which are cross-linked by the sharing of oxygen atoms. The electrovalence of each tetrahedron containing an aluminum atom is balanced by association with a cation. Most commonly this cation is a metal cation such as $Na^+$ or $K^+$ but organic species such as quaternary ammonium ions are also employed in zeolite synthesis and in some instances appear as cations in the synthesized product zeolite. In general the metal cations are, to a considerable extent at least, replaceable with other cations including $H^+$ and $NH_4^+$. In many instances the organic cation species are too large to pass through the pore system of the zeolite and hence cannot be directly replaced by ion exchange techniques. Thermal treatments can reduce these organic cations to $H^+$ or $NH_4^+$ cations which can be directly ion-exchanged. Thermal treatment of the $H^+$ or $NH_4^+$ cationic forms of zeolites can result in the substantial removal of these cations from their normal association with the $AlO_4^-$ tetrahedra thereby creating an electrovalent imbalance in the zeolite structure which must be accompanied by structural rearrangements to restore the electrovalent balance. Commonly when $AlO_4^-$ tetrahedra constitute about 40% or more of the total framework tetrahedra, the necessary structural rearrangements cannot be accommodated and the crystal structure collapses. In more siliceous zeolites, the structural integrity is substantially maintained but the resulting "decationized" form has certain significantly different properties from its fully cationized precursor.

The relative instability of aluminum in zeolites, particularly in the non-metallic cationic or the decationized form, is well recognized in the art. For example, in U.S. Pat. No. 3,640,681, issued to P. E. Pickert on Feb. 3, 1972, there is disclosed a process for extracting framework aluminum from zeolites which involves dehydroxylating a partially cation deficient form of the zeolite and then contacting it with acetylacetone or a metal derivative thereof to chelate and solubilize aluminum atoms. Ethylenediaminetetraacetic acid has been proposed as an extractant for extracting aluminum from a zeolite framework in a process which is in some respects similar to the Pickert process. It is also known that calcining the $H^+$ or $NH_4^+$ cation forms of zeolites such as zeolite Y in an environment of water vapor, either extraneous or derived from dehydroxylation of the zeolite itself, is effective in removing framework aluminum by hydrolysis. Evidence of this phenomenon is set forth in U.S. Pat. No. 3,506,400, issued Apr. 14, 1970 to P. E. Eberly, Jr. et al.; U.S. Pat. No. 3,493,519, issued Feb. 3, 1970 to G. T. Kerr et al.; and U.S. Pat. No. 3,513,108, issued May 19, 1970 to G. T. Kerr. In those instances in which the crystal structure of the product composition is retained after the rigorous hydrothermal treatment involved, infrared analysis indicated the presence of substantial hydroxyl groups exhibiting a stretching frequency in the area of about 3740, 3640 and 3550 $cm^{-1}$. The infrared analytical data of U.S. Pat. No. 3,506,400 is especially instructive in this regard. An explanation of the mechanism of the creation of these hydroxyl groups is provided by Kerr et al. in U.S. Pat. No. 3,493,519 wherein the patentees states that the aluminum atoms in the lattice framework of hydrogen zeolites can react with water resulting in the removal of aluminum from the lattice in accordance with the following equation:

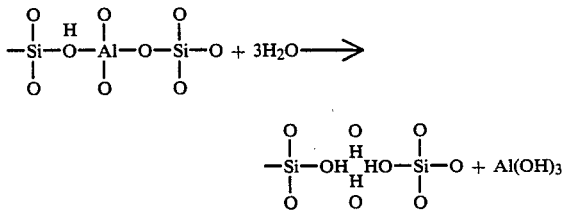

The aluminum removed from its original lattice position is capable of further reaction with cationic hydrogen, according to Kerr et al. to yield aluminum-containing i.e., hydroxyoaluminum, cations by the equation:

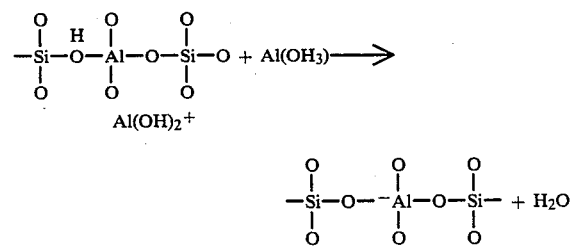

It has been suggested that stabilization of $NH_4Y$ occurs through hydrolysis of sufficient framework aluminum to form stable clusters of these hydroxoaluminum cations within the sodalite cages, thereby holding the zeolite structure together while the framework anneals itself through the migration of some of the framework silicon atoms.

It is alleged in U.S. Pat. No. 3,594,331, issued July 20, 1971 to C. H. Elliott, that fluoride ions in aqueous media, particularly under conditions in which the pH is less than about 7, are quite effective in extracting framework aluminum from zeolite lattices, and in fact when the fluoride concentration exceeds about 15 grams active fluoride per 10,000 grams of zeolite, destruction of the crystal lattice by the direct attack on the framework silicon as well as on the framework aluminum can result. A fluoride treatment of this type using from 2 to 22 grams of available fluoride per 10,000 grams of zeolite (anhydrous) in which the fluorine is provided by ammonium fluorosilicate is also described therein. The treatment is carried out for the purpose of improving the thermal stability of the zeolite. It is theorized by the patentee that the fluoride in some manner becomes attached to the constructional alkali metal oxide, thereby reducing the fluxing action of the basic structural Na₂O which would otherwise result in the collapse of the crystal structure. Such treatment within the constraints of the patent disclosure has no effect on either the overall silicon content of the zeolite product or the silicon content of a unit cell of the zeolite.

Since stability is quite obviously, in part at least, a function of the $Al_2O_3$ content of the zeolite framework, it would appear to be advantageous to obtain zeolites having lower proportions of $Al_2O_3$ while avoiding the structural changes inherent in framework aluminum extraction. Despite considerable effort in this regard, however, only very modest success has been achieved, and this has applied to a few individual species only.

A process for increasing the $SiO_2/Al_2O_3$ ratio in zeolites is disclosed in copending U.S. Ser. No. 315,853, filed Oct. 28, 1981. The process disclosed therein comprises inserting silicon atoms as $SiO_4$ tetrahedra into the crystal lattice of an aluminosilicate having a $SiO_2/Al_2O_3$ molar ratio of at least 3 and pore diameters of at least 3 Angstroms with a fluorosilicate salt in an amount of at least 0.0075 moles per 100 grams of the zeolitic aluminosilicate on an anhydrous basis, said fluorosilicate salt being in the form of an aqueous solution having a pH value within the range of 3 to about 7 and brought into contact with the zeolitic aluminosilicate at a rate sufficiently slow to preserve at least 60 percent of the crystallinity of the starting zeolitic aluminosilicate.

The difficulty which is met in preparing titanium-containing molecular sieve compositions is further demonstrated by the failure of European patent application Ser. No. 82109451.3 (Publication No. 77,522 published Apr. 27, 1983) entitled "Titanium-containing zeolites and method for their production as well as use of said zeolites", to actually prepare titanium-containing molecular sieve compositions. Although the applicants claim the preparation of titano-aluminosilicates having the pentasil structure, it is evident from an analysis of the products of the examples that titanium was not present in the form of a framework tetrahederal oxide. The products of the examples of European patent application Ser. No. 82109451.3 will be discussed in detail in comparative examples hereinafter.

SUMMARY OF THE IVENTION

Figure 1:
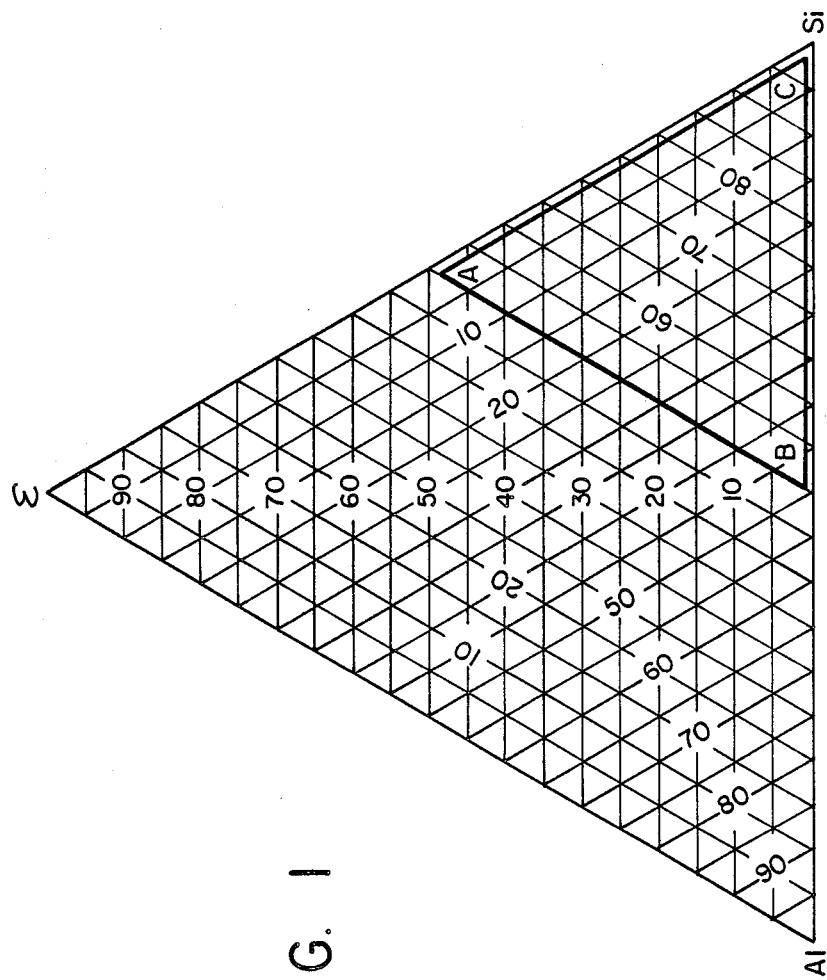
FIG. 1 is a tertnary diagram wherein parameters relating to the instant compositions are set forth as mole fractions.

Molecular sieves and the process for their preparation are claimed wherein said molecular sieves have three-dimensional microporous crystalline framework structures of $TiO_2$ and/or $FeO_2$, $AlO_2$ and $SiO_2$ tetrahedral oxide units. These new molecular sieves have a unit empirical formula on an anhydrous basis of:

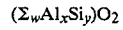

$$(\Sigma_wAl_xSi_y)O_2$$

where "$\Sigma$" is at least titanium and/or iron; and "w", "x" and "y" represent one of the mole fractions of "$\Sigma$", aluminum and silicon, respectively, present as framework tetrahedral oxide units, said mole fractions being such that they are within the compositional area defined by points A, B and C in FIG. 1, where points A, B and C have the following values for "w", "x" and "y":

| | Mole Fraction | | |
| Point | w | x | y |
| --- | --- | --- | --- |
| A | 0.49 | 0.01 | 0.50 |
| B | 0.01 | 0.49 | 0.50 |
| C | 0.01 | 0.01 | 0.98 |

DETAILED DESCRIPTION OF THE INVENTION

The present invention relates to new molecular sieve compositions and to the processes for their preparation. The molecular sieves of the instant invention have three-dimensional microporous crystal framework structures of "$\Sigma O_2$", $AlO_2$ and $SiO_2$ tetrahedral units which have a unit empirical formula on an anhydrous basis of:

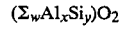

$$(\Sigma_wAl_xSi_y)O_2 \qquad (1)$$

wherein "$\Sigma$" represents at least one of titanium and/or iron; and "w", "x" and "y" represent the mole fractions of "$\Sigma$", aluminum and silicon, respectively, present as tetrahedral oxides, said mole fractions being such that they are within the trigonal compositional area defined by points A, B and C and representing the following values for "w", "x", and "y":

| | Mole Fraction | | |
| Point | w | x | y |
| --- | --- | --- | --- |
| A | 0.49 | 0.01 | 0.50 |
| B | 0.01 | 0.49 | 0.50 |
| C | 0.01 | 0.01 | 0.98 |

The term "unit empirical formula" is used herein according to its common meaning to designate the simplest formula which gives the relative number of moles of titanium and/or iron, aluminum and silicon which form "$\Sigma O_2$", $AlO_2$, and $SiO_2$ tetrahedral units within the molecular sieve. The unit emprical formula is given in terms of titanium and/or iron, aluminum and silicon as shown in Formula (1), above, and does not include other compounds, cations or anions which may be present as a result of the preparation or the existence of other impurities or materials in the bulk composition not containing the aforementioned tetrahedral units.

The instant process generally comprises a method for removing framework aluminum from zeolites having $SiO_2/Al_2O_3$ mole ratios of about 3 or greater and substituting therefore one or more elements selected from the group consisting of titanium and iron. The resulting molecular sieves contain titanium and/or iron and have crystal structures similar to that of the initial zeolite.

The process of the invention comprises contacting a crystalline zeolite having pore diameters of at least about 3 Angstroms and having a molar $SiO_2/Al_2O_3$ ratio of at least 3, with an effective amount of fluoro salt of titanium and/or iron, preferably in an amount of at least 0.001 moles per 100 grams of zeolite starting material, said fluoro salt being in the form of an aqueous solution or slurry and brought into contact with the zeolite either incrementally or continuously at a slow rate (optionally in the presence of a buffer) whereby framework aluminum atoms of the zeolite are removed and replaced by titanium and/or iron atoms. It is desirable that the process be carried out such that at least 60, preferably at least 80, and more preferably at least 90 percent of the crystal structure of the starting zeolite is retained and that the Defect Structure Factor (hereinafter defined) is increased by less than 0.15, and preferably by less than 0.10.

Crystalline zeolite starting materials suitable for the practice of the present invention can be any of the well known naturally occurring or synthetically produced zeolite species which have pores large enough to permit the passage of water, titanium and/or iron fluoro salts and reaction products through their internal cavity system. These materials can be represented, in terms of molar ratios of oxides, as $$M_{2/n}O \cdot Al_2O_3 : xSiO_2 : yH_2O$$

wherein "M" is a cation having the valence "n", "x" is a value of at least about 3 and "y" has a value of from zero to about 9 depending upon the degree of hydration and the capacity of the particular zeolite to hold absorbed water. Alternatively, the framework composition of the naturally occurring or synthetic zeolite starting material can be expressed in terms of the mole fraction of framework tetrahedra, $TO_2$, as:

$$(Al_a Si_b)O_2 \qquad (2)$$

wherein "a" is the fraction of framework tetrahedral sites occupied by aluminum atoms and "b" is the fraction of framework tetrahedral sites occupied by silicon atoms. Should the framework of the starting material contain atoms in addition to silicon and aluminum, these materials may be similarly expressed in terms of their "$TO_2$" formula in terms of their fractional occupation of the framework of the starting material. The algebraic sum of all of the subscripts within the brackets is equal to 1. In the above example, $a + b = 1$.

Representative of the crystalline aluminsilicate zeolite molecular sieves which may be employed in the instant process include, but are not limited to erionite, mordenite, clinoptilolite, zeolite Y, zeolite L, zeolite LZ-105, zeolite omega, zeolite beta, zeolite TMA offretite, zeolite ZSM-5, zeolite ZSM-34 and zeolite ZSM-35. Both naturall;y occurring and synthetically prepared zeolite molecular sieves can be used. Zeolite Y is disclosed in U.S. Pat. No. 3,130,007; zeolite L is disclosed in U.S. Pat. No. 3,216,789; zeolite LZ-105 is disclosed in U.S. Pat. No. 4,257,885; zeolite omega is disclosed in U.S. Pat. No. 4,241,036; zeolite beta is disclosed in U.S. Pat. No. 3,308,069; zeolite ZSM-5 is disclosed in U.S. Pat. No. 3,702,886; zeolite ZSM-34 is disclosed in U.S. Pat. No. 4,086,186; and zeolite ZSM-35 is disclosed in U.S. Pat. No. 3,992,466.

For reasons more fully explained hereinafter, the starting zeolite should be able to withstand the initial loss of framework aluminum atoms to at least a modest degree without collapse of the crystal structure unless the process is to be carried out at a very slow rate. In general the ability to withstand aluminum extraction and maintain a high level of crystallinity is directly proportional to the initial $SiO_2/Al_2O_3$ molar ratio of the zeolite. Accordingly, it is preferred that the value for "x" in the formula above, be at least about 3. Also it is preferred that at least about 50, and more preferably at least 95% of the $AlO_4$ tetrahedra of the naturally occurring or as-synthesized zeolite are present in the staring zeolite. Most advantageously the starting zeolite contains as many as possible of its original $AlO_4$ tetrahedra, i.e. has not been subjected to any post-formation treatment which either extensively removes aluminum atoms from their original framework sites or converts them from the normal conditions of 4-fold coordination with oxygen.

The cation population of the starting zeolite is not a critical factor insofar as substitution of titanium and/or iron for framework aluminum is concerned, but since the substitution mechanism may involve the in situ formation of salts of at least some of the zeolitic cations, it is advantageous that these salts be water-soluble to a substantial degree to facilitate their removal from the molecular sieve product. It is found that ammonium cations form the most soluble salts in this regard and it is accordingly preferred that at least 50 percent, most preferably 85 or more percent, of the zeolite cations be ammonium or hydronium cations. Sodium and potassium, two of the most common cations present in zeolites, are found to form $Na_3AlF_6$ and $K_3AlF_6$ respectively, both of which are only very sparingly soluble in either hot or cold water. When these compounds are formed as precipitates within the structural cavities of the zeolite they are quite difficult to remove by water washing. Their removal, moreover, is important if thermal stability of the molecular sieve product is desired since substantial amounts of fluoride can cause crystal collapse at temperatures as low as 500° C.

For purposes of simplifying the description of the products of the above process, as above defined the framework composition of the zeolite starting material and the products of the instant process are expressed in terms of mole fractions of framework tetrahedra, i.e., the "$TO_2$". The starting zeolite may be expressed as:

$$(Al_a Si_b \square_z)O_2$$

whereas "a" is the mole fraction of aluminum tetrahedra in the framework; "b" is the mole fraction of silicon tetrahedra in the framework; "$\square$" denotes defect sites in the framework; and "z" is the mole fraction of defect sites in the zeolite framework. In many cases the "z" value for the starting zeolite is zero and the defect sites are simply eliminated from the expression. Numerically the sum of the values $a + b + z = 1$.

The molecular sieves products of the instant process, expressed in terms of the mole fractions of framework tetrahedra ($TO_2$) will have the form:

$$[Al_{(a-N)} Si_b \Sigma_c \square_z]O_2$$

wherein: "N" is defined as the mole fraction of aluminum tetrahedra removed from the framework during the treatment; "a" is the mole fraction of aluminum tetrahedra present in the framework of the starting zeolite; "b" is the mole fraction of silicon tetrahedra present in the framework of the starting zeolite; "z" is the mole fraction of defect sites in the framework; the Greek letter sigma, "$\Sigma$" denotes at least one of titanium and iron; and "c" is the mole fraction of titanium and/or iron tetrahedra resulting from the fluoro salt treatment of the instant process. Theoretically, there should be no change in the silicon content and therefore "c" should equal $(N-\Delta z)$ where "$\Delta z$" is the net change in the mole fraction of defect sites in the zeolite framework resulting from the treatment, $\Delta z = z$ (product zeolite) $- z$ (starting zeolite) The term "Defect Structure Factor" value of that particular zeolite. The net change in Defect Structure Factors between the starting zeolite and the product zeolite is equivalent to "$\Delta z$". Numerically, the sum of the values:

$$(a-N)+b+c+z=1;$$

and $$(a-N)+b+(N-\Delta z)+z=1$$

The titanium and iron-containing molecular sieve compositions prepared by the instant process have framework aluminum removed from the starting zeolite with substitution therefore by titanium and/or iron. The instant process generally comprises contacting a crystalline zeolite having a pore diameter of at least about 3 Angstroms and having a molar $SiO_2/Al_2O_3$ ratio of at least 3, with an effective amount of a fluoro salt of titanium and/or iron, preferably an amount of at least 0.001 moles of fluoro salt per 100 grams of zeolite starting material, said fluoro salt being in the form of a solution or slurry, preferably aqueous and/or alcohols, at an effective pH where the pH value is generally greater than one (1), more preferably greater than 3 and most preferably in the range of about 3 to about 7. The fluoro salt solution or slurry is brought into contact with the zeolite either incrementally or continuously at a slow rate whereby framework aluminum atoms of the zeolite are removed and replaced by titanium and/or iron atoms from the fluoro salt. The fluoro salt is preferably provided as an aqueous solution or slurry but it is believed that solutions or slurries employing alcohols and other organic solvents may be employed.

The process generally comprises:

(a) contacting at effective process conditions a zeolite with an effective amount of a fluoro salt of titanium and/or iron; and (b) isolating the titanium and/or iron-containing molecular sieve product from the reaction mixture.

The fluoro salt is in the form of a solution or slurry, preferably aqueous, and is brought into contact with the zeolite either incrementally or continuously at an effective rate such that a portion of the framework aluminum atoms are removed and replaced by titanium and/or iron atoms at a rate which preferably retains at least 80 percent and more preferably at least 90 percent of the crystal structure of the starting zeolite.

For reasons more fully explained hereinafter, the starting zeolite should be able to withstand the initial loss of framework aluminum atoms to at least a modest degree without collapse of the crystal structure unless the process is to be carried out at a very slow pace, or the process is to be buffered as hereinbefore discussed. Accordingly, the $SiO_2/Al_2O_3$ ratio in the initial Y zeolite starting material is preferably at least about 3.0. It is preferred that at least about 50%, and more preferably at least 95%, of the $AlO_4^-$ tetrahedra of the naturally occurring or as-synthesized synthetic zeolite are present in the starting zeolite, i.e., the starting zeolite has not been subjected to any post-formation treatment which either extensively removes aluminum atoms from their original framework sites or converts them from the normal conditions of 4-fold coordination with oxygen.

The fluoro salt used as the aluminum extractant and also as the source of titanium and/or iron, which is inserted into the zeolite structure in place of the extracted aluminum, can be any of the fluoro salts having the general formula:

$$(A)_{2/b}\Sigma F_6; (A)_{2/b}\Sigma F_5; \text{ or } (A)_{2/b}\Sigma F_4$$

wherein "$\Sigma$" is titanium and/or iron and "A" is a metallic or non-metallic cation, having the valence "b". Cations represented by "A" include alkylammonium, $NH_4^+$, $H^+$, $Mg^{++}$, $Li^+$, $Na^+$, $K^+$, $Ba^{++}$, $Cd^{++}$, $Cu^+$, $Cu^{++}$, $Ca^{++}$, $Cs^+$, $Fe^{++}$, $Co^{++}$, $Pb^{++}$, $Mn^{++}$, $Rb^+$, $Ag^+$, $Sr^{++}$, $Tl^+$ and $Zn^{++}$. The ammonium cation form of the fluoro salt is generally preferred because of its solubility in water and also because the ammonium cations form water soluble by-product salts upon reaction with the zeolite, namely $(NH_4)_3AlF_6$ and/or $(NH_4)_2AlF_5$.

The manner in which the fluoro salt of titanium and/or iron and the starting zeolite are brought into contact and the overall process of substituting titanium and/or iron for aluminum in the zeolite framework is believed to be a two step process in which the aluminum extraction step tends to, unless controlled, proceed very rapidly while the insertion of titanium and/or iron is generally relatively slow. If dealumination becomes too extensive without the substitution of titanium and/or iron the crystal structure becomes seriously degraded and ultimately collapses. While not wishing to be bound by any particular theory, it appears that fluoride ion acts as the agent for extraction of framework aluminum in accordance with the equation:

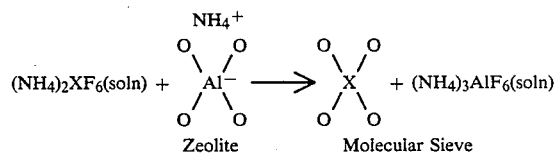

It is important, therefore, that the initial dealumination step be inhibited and the step involving insertion of titanium and/or iron be promoted to achieve the desired molecular sieve products. It is found that the various zeolites have varying degrees of resistance toward degradation as a consequence of framework aluminum extraction without substitution of titanium and/or iron into the framework. The rate of aluminum extraction generally decreases as the pH of the fluoro salt solution in contact with the zeolite is increased below about one (1) (and accordingly the pH is preferably within the range of 3 to 7) and as the concentration of the fluoro salt of titanium and/or iron in the reaction system is decreased. Also, increasing the reaction temperature tends to increase the rate of substitution of titanium and/or iron. Whether it is necessary or desirable to buffer the reaction system or select a particular fluoro salt concentration to control the pH it is readily determined for each zeolite species by routine observation and evaluation. The question of whether the reaction system may advantageously be buffered will in large part depend on the selection of the particular starting zeolite, since zeolites have varying tolerances to acid and base media. For example, some zeolites can withstand very low pH conditions and a high level of dealumination without collapse of the crystal structure. When it is advantageous to buffer the reaction mixture in a particular pH range the reaction mixture may be buffered in a manner as generally heretofore employed in the art. The use of buffering salts, such as ammonium acetate, or use of an inert solid to react with excess acid or base, e.g. clays or aluminas, may be generally employed to buffer the pH of the reaction mixture.

Theoretically, there is no lower limit for the concentration of fluoro salt of titanium and/or iron in the aqueous solution or slurry employed, provided of course the effective pH (the "effective pH" is a pH such that under effective process conditions a monomeric form of titanium is present in the reaction system) of the solution or slurry is high enough to avoid undue destructive acidic attack on the particular zeolite structure apart from the intended reaction with an effective amount of the fluoro salt, i.e. that amount which provides sufficient fluoride and amount of titanium and/or iron for the process and desired amount of titanium and/or iron in the final molecular sieve product. A slow rate of addition of the fluoro salt generally provides adequate time for the insertion of titanium and/or iron as a framework substitute for extracted aluminum before excessive aluminum extraction occurs with consequent collapse of the crystal structure. Practical commercial considerations, however, may require that the reaction proceed as rapidly as possible, and accordingly the conditions of reaction temperature and reagent concentrations will necessarily be optimized with respect to each zeolite starting material and with respect to commercial operation. In general it is believed that the more highly siliceous the zeolite, the higher the permissible reaction temperature and the lower the pH conditions which may be employed in the instant process. In general the preferred effective reaction temperature is within the range between about 10° and about 99° C., preferably between about 20° C. and 95° C., but temperatures of 125° C. or higher and as low as 0° C. are believed employable in some instances with some zeolite starting materials and with fluoro salts in a form other than aqueous solutions or slurries. At pH values below about 3 crystal degradation of many zeolites is found to be unduly severe, whereas at pH values higher than 7, insertion of the titanium and/or iron may be slow from a practical standpoint as a result of the solubility of titanium and iron at these pHs and as a result of certain polymerization reactions. The maximum concentration of fluoro salt in the aqueous solution employed is, of course, interrelated to the temperature and pH factors and also with the time of contact between the zeolite and the solution and the relative proportions of zeolite and fluoro salt. Solutions having fluoro salt concentrations of between about $10^{-3}$ moles per liter of solution and up to saturation of the solution can be employed, but it is preferred that concentrations in the range of between about 0.5 and about 1.0 moles per liter of solution be used. In addition, as hereinbefore discussed, slurries of the fluoro salts of titanium and/or iron may be employed. The aforementioned concentration values are with respect to true solutions, and are not intended to apply to the total fluoro salts in solution or in slurries of the salts in water. Even very slightly soluble fluoro salts can be slurried in water and used as a reagent—the undissolved solids being readily available to replace dissolved molecular species consumed in reaction with the zeolite. As stated hereinabove, the amount of dissolved fluoro salts employed with respect to the particular zeolite being treated will depend to some extent upon the physical and chemical properties of the individual zeolites and other effective process conditions. However, the minimum value for the amount of fluoro salt to be added is preferably at least equivalent to the minimum mole fraction of aluminum to be removed from the zeolite.

In specifying the proportions of the zeolite starting material or adsorption properties of the zeolite product and the like herein, the "anhydrous state" of the zeolite will be intended unless otherwise stated. The term "anhydrous state" is employed herein to refer to a material substantially devoid of both physically adsorbed and chemically adsorbed water. In general a zeolite may be prepared in the anhydrous state by heating the zeolite in dry air at about 450° C. for about 4 hours.

It is apparent from the foregoing that, with respect to effective process conditions, it is desirable that the integrity of the zeolite crystal structure be substantially maintained throughout the process, and that, in addition to having titanium and/or iron atoms inserted into the lattice, the zeolite retains at least 60 percent, preferably at least 80 and more preferably at least 90 percent of its original crystallinity. A convenient technique for assessing the crystallinity of the products relative to the crystallinity of the starting material is the comparison of the relative intensities of the d-spacings of their respective X-ray powder diffraction patterns. The sum of the peak heights, in terms of arbitrary units above background, of the starting material is used as the standard and is compared with the corresponding peak heights of the products. When, for example, the numerical sum of the peak heights of the molecular sieve product is 85 percent of the value of the sum of the peak heights of the starting zeolite, then 85 percent of the crystallinity has been retained. In practice it is common to utilize only a portion of the d-spacing peaks for this purpose, as for example, five of the six strongest d-spacings. In zeolite Y these d-spacings correspond to the Miller Indices 331, 440, 533, 642 and 555. Other indicia of the crystallinity retained by the zeolite product are the degree of retention of surface area and the degree of retention of the adsorption capacity. Surface areas can be determined by the well-known Brunauer-Emmett-Teller method (B-E-T). J. Am. Chem. Soc. 60 309 (1938) using nitrogen as the adsorbate. In determining the adsorption capacity, the capacity for oxygen at −183° C. at 100 Torr is preferred.

All available evidence, to date, indicates that the above described process of this invention is unique in being able to produce zeolites essentially free of defect structure and having titanium and/or iron inserted into the framework by a secondary synthesis process.

In untreated, i.e. naturally occurring or as-synthesized zeolites the original tetrahedral structure is conventionally represented as

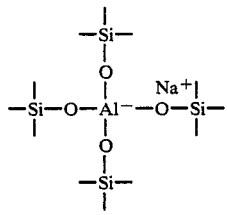

After treatment with a complexing agent such as ethylene-diaminetetraacetic acid (H$_4$EDTA) in which a stoichiometric reaction occurs whereby framework aluminum atoms along with an associated cation such as sodium is removed as NaAlEDTA, it is postulated that the tetrahedral aluminum is replaced by four protons which form a hydroxyl "nest", as follows:

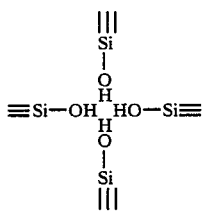

The infrared spectrum of the aluminum depleted zeolite will show a broad nondescript absorption band beginning at about 3750 cm$^{-1}$ and extending to about 3000 cm$^{-1}$. The size of this absorption band or envelope increases with increasing aluminum depletion of the zeolite. The reason that the absorption band is so broad and without any specific absorption frequency is that the hydroxyl groups in the vacant sites in the framework are coordinated in such a way that they interact with each other (hydrogen bonding). The hydroxyl groups of adsorbed water molecules are also hydrogen-bonded and produce a similar broad absorption band as do the "nest" hydroxyls. Also, certain other zeolitic hydroxyl groups, exhibiting specific characteristic absorption frequencies within the range of interest, will if present, cause infrared absorption bands in these regions which are superimposed on the band attributable to the "nest" hydroxyl groups. These specific hydroxyls are created by the decomposition of ammonium cations or organic cations present in the zeolite.

It is, however, possible to treat zeolites, prior to subjecting them to infrared analysis, to avoid the presence of the interfering hydroxyl groups and thus be able to observe the absorption attributable to the "nest" hydroxyls only. The hydroxyls belonging to adsorbed water are avoided by subjecting the hydrated zeolite sample to vacuum activation at a moderate temperature of about 200° C. for about 1 hour. This treatment permits desorption and substantially complete removal of the adsorbed water. Complete removal of adsorbed water can be ascertained by noting when the infrared absorption band at about 1640 cm$^{-1}$, the bending frequency of water molecules, has been removed from the spectrum.

The decomposable ammonium cations can be removed, at least in large part, by ion-exchange and replaced with metal cations, preferably by subjecting the ammonium form of the zeolite to a mild ion exchange treatment with an aqueous NaCl solution. The OH absorption bands produced by the thermal decomposition of ammonium cations are thereby avoided. Accordingly the absorption band over the range of 3745 cm$^{-1}$ to about 3000 cm$^{-1}$ for a zeolite so treated is almost entirely attributable to hydroxyl groups associated with defect structure and the absolute absorbance of this band can be a measure of the degree of aluminum depletion.

It is found, however, that the ion-exchange treatment, which must necessarily be exhaustive even though mild, required considerable time. Also the combination of the ion-exchange and the vacuum calcination to remove adsorbed water does not remove every possible hydroxyl other than defect hydroxyls which can exhibit absorption in the 3745 cm$^{-1}$ to 3000 cm$^{-1}$ range. For instance, a rather sharp band at 3745 cm$^{-1}$ has been attributed to the Si-OH groups situated in the terminal lattice positions of the zeolite crystals and to amorphous (non-zeolitic) silica from which physically adsorbed water has been removed. For these reasons we prefer to use a somewhat different criterion to measure the degree of defect structure in the zeolite products of this invention.

In the absence of hydrogen-bonded hydroxyl groups contributed by physically adsorbed water, the absorption frequency least affected by absorption due to hydroxyl groups other than those associated with framework vacancies or defect sites is at 3710±5 cm$^{-1}$. Thus the relative number of defect sites remaining in a zeolite product of this invention can be gauged by first removing any adsorbed water from the zeolite, determining the value of the absolute absorbance in its infrared spectrum at a frequency of 3710 cm$^{-1}$, and comparing that value with the corresponding value obtained from the spectrum of a zeolite having a known quantity of defect structure. The following specific procedure has been arbitrarily selected and used to measure the amount of defect structure in the products prepared in the Examples appearing hereinafter. Using the data obtained from this procedure it is possible, using simple mathematical calculation, to obtain a single and reproducible value hereinafter referred to as the "Defect Structure Factor", denoted hereinafter by the symbol "z", which can be used in comparing and distinguishing the present novel zeolite compositions from their non-titanium and/or iron containing counter-parts.

DEFECT STRUCTURE FACTOR "Z"

(A) Defect Structure Zeolite Standard

Standards with known amounts of defect structure can be prepared by treating a crystalline zeolite of the same species as the product sample with ethylenediaminetetraacetic acid by the standard procedure of Kerr as described in U.S. Pat. No. 3,442,795. In order to prepare the standard it is important that the starting zeolite be well crystallized, substantially pure and free from defect structure. The first two of these properties are readily determined by conventional X-ray analysis and the third by infrared analysis using the procedure set forth in part (B) hereof. The product of the aluminum extraction should also be well crystallized and substantially free from impurities. The amount of aluminum depletion, i.e., the mole fraction of tetrahedral defect structure of the standard samples can be ascertained by conventional chemical analytical procedure. The molar SiO$_2$/Al$_2$O$_3$ ratio of the starting zeolite used to prepare the standard sample in any given case is not narrowly critical, but is preferably within about 10% of the molar $SiO_2/Al_2O_3$ ratio of the same zeolite species used as the starting material in the practice of the process of the present invention.

(B) Infrared Spectrum of Product Samples and Defect Structure Zeolite Standard

Fifteen milligrams of the hydrated zeolite to be analyzed are pressed into a 13 mm. diameter self-supporting wafer in a KBr die under 5000 lbs. pressure. The wafer is then heated at 200° C. for 1 hour at a pressure of not greater than $1\times 10^{-4}$ mm. Hg to remove all observable traces of physically adsorbed water from the zeolite. This condition of the zeolite is evidenced by the total absence of an infrared absorption band at 1640 cm$^{-1}$. Thereafter, and without contact with adsorbable substances, particularly water vapor, the infrared spectrum of the wafer is obtained on an interferometer system at 4 cm$^{-1}$ resolution over the frequency range of at least 3745 to 3000 cm$^{-1}$. Both the product sample and the standard sample are analyzed using the same interferometer system to avoid discrepancies in the analysis due to different apparatus. The spectrum, normally obtained in the transmission mode of operation is mathematically converted to and plotted as wave number vs. absorbance.

(C) Determination of the Defect Structure Factor

The defect structure factor (z) is calculated by substituting the appropriate data into the following formula:

$$z = \frac{AA_{(ps)} \times \text{(Mole fraction of defects in the standard)}}{AA_{(std)}}$$

wherein $AA_{(ps)}$ is the infrared absolute absorbance measured above the estimated background of the product sample at 3710 cm$^{-1}$; $AA_{(std)}$ is the absolute absorbance measured above the background of the standard at 3710 cm$^{-1}$ and the mole fraction of defects in the standard are determined in accordance with part (A) above.

Once the defect structure factor, z, is known, it is possible to determine from the wet chemical analysis of the product sample for $SiO_2$, $Al_2O_3$, titanium and/or iron and the cation content as $M_{2/n}O$ whether titanium and/or iron has been substituted for aluminum in the zeolite as a result of the treatment and also the efficiency of the substitution of titanium and/or iron.

The essential X-ray powder diffraction patterns appearing in this specification and referred to in the appended claims are obtained using either: (1) standard X-ray powder diffraction techniques; or (2) computer based techniques using copper K-alpha radiation and using Siemens D-500 X-ray powder diffractometers with Siemens Type K-805 X-ray sources, available from Siemens Corporation, Cherry Hill, New Jersey, with appropriate computer interface. When employing the standard X-ray technique the radiation source is a high-intensity, copper target, x-ray tube operated at 50 Kv and 40 ma. The diffraction pattern from the copper K alpha radiation and graphite monochromator is suitably recorded by an X-ray spectrometer scintillation counter, pulse-height analyzer and strip-chart recorder. Flat compressed powder samples are scanned at 2° (2 theta) per minute, using a 2 second time constant. Interplanar spacings (d) are obtained from the position of the diffraction peaks expressed as 2 theta, where 2 theta is the Bragg angle as observed on the strip chart. Intensities are determined from the heights of diffraction peaks after subtracting background.

In determining the cation equivalency, i.e. the molar ratio $M_{2/n}O/Al_2O_3$. in each zeolite product, it is advantageous to perform the routine chemical analysis on a form of the zeolite in which "M" is a monovalent cation other than hydrogen. This avoids the uncertainty which can arise in the case of divalent or polyvalent metal zeolite cations as to whether the full valence of the cation is employed in balancing the net negative charge associated with each $AlO_4^-$ tetrahedron or whether some of the positive valence of the cation is used in bonding with $OH^-$ or $H_3O^+$ ions.

The following examples are provided to illustrated the invention and are not intended to be limiting thereof:

EXAMPLE 1

(1) Ten grams (gm) of an ammonium-exchanged zeolite Y containing 43.5 millimoles of aluminum, as $Al_2O_3$, were slurried in 100 milliliters (ml) of an aqueous 3.5 molar solution of ammonium acetate at a temperature of 75° C. Because of the limited solubility of $(NH_4)_2TiF_6$, the fluoro salt was added to the slurry as crystals. The weight of added $(NH_4)_2TiF_6$ was 4.78 grams. The amount of fluoro salt is an amount sufficient to replace 55% of the aluminum of the zeolite with titanium. The resulting reaction mixture was then digested for 17 hours at 75° C. The reaction mixture was then filtered and washed with warm distilled water until qualitative testing of the wash water was negative for both aluminum and fluoride ions. The chemical analyses for the starting zeolite Y and the molecular sieve product prepared therefrom (hereinafter referred to as "LZ-225") are set forth in Table 1:

TABLE 1

| | Starting Zeolite Y | LZ-225 Product |
|---|---|---|
| $Na_2O$, wt. % | 2.53 | 1.56 |
| $(NH_4)_2O$, wt % | 9.51 | 4.50 |
| $TiO_2$, wt % | — | 16.23 |
| $Al_2O_3$, wt % | 22.18 | 10.00 |
| $SiO_2$, wt % | 64.38 | 63.75 |
| $F_2$, wt % | — | 0.10 |
| $SiO_2/Al_2O_3$ | 4.93 | 10.82 |
| $Na^+/Al$ | 0.19 | 0.26 |
| $NH_4^+/Al$ | 0.84 | 0.80 |
| Cation Equivalent, $M^+/Al$ | 1.03 | 1.06 |
| $Si/(Al_2 + Ti_2)$ | 4.93 | 5.31 |

A comparison of the properties of the LZ-225 product with the starting Zeolite Y is shown in Table 2.

TABLE 2

| | Starting Zeolite Y | LZ-225 Product |
|---|---|---|
| X-Ray Crystallinity, | | |
| % by Peak Intensity: | 100 | 48 |
| Unit Cell, $a_o$ in Å: | 24.712 | 24.590 |
| Crystal Collapse Temp. °C. (DTA): | 890 | 962 |
| Framework Infrared: | | |
| Asymmetric Stretch, cm$^{-1}$: | 1015 | 1031 |
| Symmetric Stretch, cm$^{-1}$: | 789 | 794 |
| Hydroxyl Infrared: | | |
| Absolute Absorbance at 3710cm$^{-1}$: | 0.020 | 0.194 |
| Defect Structure Factor, z: | 0.009 | 0.082 |
| McBain Adsorption: | | |
| Wt. % $O_2$, 100 torr, | 35.2 | 28.4 |

TABLE 2-continued

|  | Starting Zeolite Y | LZ-225 Product |
|---|---|---|
| −183° C.: | | |
| Wt. % H$_2$O, 4.6 torr, 25° C.: | 32.1 | 27.6 |

(2) The framework mole fractions of tetrahedra are set forth below for the starting Zeolite Y and the LZ-225 molecular sieve product and were:
  (a) Mole fraction of Oxides (TO$_2$):
    Starting Zeolite Y: (Al$_{0.286}$Si$_{0.705}\square_{0.009}$)O$_2$
    LZ-225 Product: (Al$_{0.123}$Si$_{0.667}$Ti$_{0.128}\square_{0.082}$)O$_2$
  (b) Mole fraction of aluminum removed, N: 0.163
  (c) Percent aluminum removed, N/a×100: 57
  (d) Change in Defect Structure Factor, $\Delta$z: 0.073
  (e) Moles of titanium substituted per mole of aluminum removed: 0.79

(3) The molecular sieves denominated herein as "LZ-225" have the characteristic crystal structure of zeolite Y as indicated by an X-ray powder diffraction pattern having at least the d-spacings set forth in Table A, hereinafter, and have titanium atoms in the crystal lattice in the form of TiO$_4$ tetrahedra, preferably in an amount of at least one (1.0) TiO$_4$ tetrahedron per 10,000 Å$^3$:

TABLE A

| d,(Å) | Relative Intensity |
|---|---|
| 14.1 ± 0.2 | s |
| 8.6 ± 0.2 | m |
| 7.4 ± 0.2 | m |
| 5.6 ± 0.1 | s |
| 4.7 ± 0.1 | m |
| 4.4 ± 0.1 | m |
| 3.8 ± 0.1 | s |
| 3.3 ± 0.1 | s |
| 2.8 ± 0.1 | m |

(4) The x-ray powder diffraction pattern of the LZ-225 product when compared to a reference sample of Y shows that the peak intensities are decreased but there is no observable increase in the background due to amorphous zeolite or TiO$_2$. Since both oxygen and water capacities were essentially maintained, the decreased x-ray intensity is believed to be caused by incorporation of the titanium ion into the structure of the starting zeolite. The remaining aluminum is considered to be in the framework since the cation equivalent (M$^+$/Al) is essentially 1.0. All of the properties measured are consistent with a highly crystalline product containing about 13 mole percent titanium substituted in the zeolitic framework.

EXAMPLE 2

(1) Ten grams of an ammonium-exchanged zeolite Y containing 43.5 millimoles of aluminum as Al$_2$O$_3$, were slurried in 100 ml of an aqueous 3.5 molar solution of ammonium acetate at a temperature of 75° C. Because of the limited solubility of (NH$_4$)$_3$FeF$_6$, the salt was added to the zeolite-water slurry as crystals. The weight of added (NH$_4$)$_3$FeF$_6$ crystals was 5.41 grams and was an amount sufficient to replace 55% of the framework aluminum of the zeolite with iron. Following the addition of the (NH$_4$)$_3$FeF$_6$ crystals, the reaction mixture was digested under a nitrogen atmosphere at 75° C. for 48 hours. The reaction mixture was then filtered and washed with warm distilled water until qualitative testing of the wash water was negative for both aluminum and fluoride ions. The chemical analyses for the starting zeolite and the molecular sieve product (hereinafter referred to as "LZ-224") are set forth in Table 3:

TABLE 3

|  | Starting Zeolite Y | LZ-224 Product |
|---|---|---|
| Na$_2$O, wt. % | 2.53 | 1.60 |
| (NH$_4$)$_2$O, wt. % | 9.51 | 5.73 |
| Fe$_2$O$_3$, wt. % | — | 16.92 |
| Al$_2$O$_3$, wt. % | 22.18 | 12.60 |
| SiO$_2$, wt. % | 64.38 | 65.78 |
| F$_2$, wt. % | — | 0.20 |
| Na$^+$/Al | 0.19 | 0.21 |
| NH$_4^+$/Al | 0.84 | 0.89 |
| Cation Equivalent, M$^+$/Al | 1.03 | 1.10 |
| SiO$_2$/Al$_2$O$_3$ | 4.93 | 8.86 |
| Si/(Al$_2$ + Fe$_2$) | 4.93 | 5.77 |

A comparison of the properties of the LZ-224 molecular sieve product with the starting zeolite Y is shown in Table 4.

TABLE 4

|  | Starting Zeolite Y | LZ-224 Product |
|---|---|---|
| X-Ray Crystallinity: | | |
| % by Peak Intensity: | 100 | 36 |
| Unit Cell, a$_o$ in Å: | 24.712 | 24.636 |
| Crystal Collapse Temp. °C. (DTA): | 890 | 892 |
| Framework Infrared: | | |
| Asymmetric Stretch, cm$^{-1}$: | 1015 | 1028 |
| Symmetric Stretch, cm$^{-1}$: | 789 | 795 |
| Hydroxyl Infrared: | | |
| Absolute Absorbance at 3710 cm$^{-1}$: | 0.020 | 0.127 |
| Defect Structure Factor, z: | 0.009 | 0.054 |
| McBain Adsorption: | | |
| Wt % O$_2$, 100 torr, −183° C.: | 35.2 | 25.4 |
| Wt % H$_2$O, 4.6 torr, 25° C.: | 32.1 | 25.7 |

(2) The framework mole fraction of tetrahedra are set forth below for the starting zeolite Y and the LZ-224 molecular sieve product.
  (a) Mole fraction of Oxides (TO$_2$):
    Starting Zeolite Y: (Al$_{0.286}$Si$_{0.705}\square_{0.009}$)O$_2$
    LZ-224 Product: (Al$_{0.150}$Si$_{0.667}$Fe$_{0.129}\square_{0.054}$)O$_2$
  (b) Mole fraction of aluminum removed, N: 0.136
  (c) Percent aluminum removal, N/a×100: 48
  (d) Change in Defect Structure Factor, $\Delta$z: 0.045
  (e) Moles of titanium substituted per mole of aluminum removed: 0.95

(3) The molecular sieve's denominated herein as "LZ-224" have the characteristic crystal structure of zeolite Y as indicated by an X-ray diffraction pattern having at least the d-spacings set forth in Table B, hereinafter, and having iron atoms in the crystal lattice in the form of "FeO$_4$" tetrahedra, preferably in an amount of at least one (1.0) FeO$_4$ tetrahedron per 10,000Å$^3$:

TABLE B

| d,(Å) | Relative Intensity |
|---|---|
| 14.1 ± 0.2 | s |
| 8.6 ± 0.2 | m |
| 7.4 ± 0.2 | m |
| 5.6 ± 0 1 | m |
| 4.7 ± 0.1 | m |
| 4.4 ± 0.1 | m |
| 3.8 ± 0.1 | m |

TABLE B-continued

| d,(Å) | Relative Intensity |
|---|---|
| 3.3 ± 0.1 | m |
| 2.8 ± 0.1 | m |

(4) In the present example there were no extraneous peaks observed in the powder pattern of the LZ-224 product. The zeolite peaks were somewhat broadened and substantially decreased in intensity as compared to zeolite Y. There appears to be no overall increase in background due to amorphous material. Since both oxygen and water capacities are essentially maintained, as compared with the starting zeolite, the decreased x-ray peak intensity is believed to be caused by incorporation of iron into zeolite structure of LZ-224.

The above properties are consistent with a highly crystalline molecular sieve product containing 10 mole percent iron in the framework and additional iron in a cationic form.

EXAMPLE 3

(1) Twenty-five grams of a hydronium-exchanged synthetic mordenite (ZEOLON ( TM ), is a trademark of Norton Co.), containing 52.8 millimoles of aluminum as $Al_2O_3$ were slurried in 450 ml distilled $H_2O$. Because of the limited solubility of $(NH_4)_2TiF_6$, the salt was added to the slurry as crystals. The weight of added $(NH_4)_2TiF_6$ was 2.61 grams. This is an amount which is sufficient to replace 25% of the framework aluminum of the zeolite with titanium. The reaction mixture was then digested at reflux for 18 hours, filtered and washed with warm distilled water until testing of the wash water was negative for both aluminum and fluoride ions. The chemical analyses for the starting mordenite and the titanium-containing molecular sieve product (hereinafter referred to as "LZ-227") are set forth in Table 5 wherein this LZ-227 product is designated product A. A comparison of the properties of this LZ-227 product (Product A) with the starting mordenite is shown in Table 6. The framework mole fractions of tetrahedra are set forth below for the starting mordenite and the LZ-227 molecular sieve product:

(a) Mole fraction of Oxides ($TO_2$):
Starting mordenite: $(Al_{0.106}Si_{0.740}\square_{0.154})O_2$
LZ-227 Product A: $(Al_{0.072}Si_{0.804}Ti_{0.034}\square_{0.090})O_2$
(b) Mole fraction of aluminum removed, N: 0.034
(c) Percent aluminum removal, N/a×100: 32
(d) Change in Defect Structure Factor, $\Delta z$: −0.064
(e) Moles of titanium substituted per mole of aluminum removed: 1.00

(2) Twenty-five grams of a hydronium-exchanged synthetic mordenite (ZEOLON ( TM ), from Norton Co.), containing 52.8 millimoles of aluminum, as $Al_2O_3$ were slurried in 450 ml of distilled $H_2O$. Due to the limited solubility of $(NH_4)_2TiF_6$, the salt was added to the slurry as crystals. The weight of added $(NH_4)_2TiF_6$ was 5.22 grams and was an amount sufficient to replace 50% of the framework aluminum of the zeolite with titanium The reaction mixture was then digested at reflux for 30 minutes, filtered and washed with warm distilled water until testing of the wash water was negative for both aluminum and fluoride ions. The chemical analyses for the starting mordenite and the molecular sieve product (herein referred to as LZ-227) are set forth in Table 5 wherein this LZ-227 product is designated product B. A comparison of the properties of this LZ-227 product (Product B) with the starting mordenite and Product A is shown in Table 6. The framework mole fractions of tetrahedra are set forth below for the starting mordenite and the LZ-227 molecular sieve product:

(a) Mole fraction of Oxides ($TO_2$):
Starting H Mordenite: $(Al_{0.106}Si_{0.740}\square_{0.154})O_2$
LZ-227 Product B: $(Al_{0.069}Si_{0.748}Ti_{0.023}\square_{0.160})O_2$
(b) Mole fraction of aluminum removed, N: 0.037
(c) Percent aluminum removal, N/a×100: 35
(d) Change in Defect Structure Factor, $\Delta z$: 0.006
(e) Moles of titanium substituted per mole of aluminum removed: 0.62

(3) Twenty-five grams of a hydronium-exchanged synthetic mordenite (ZEOLON ( TM ), a trademark of Norton Co.), containing 52.8 millimoles of aluminum as $Al_2O_3$, were slurried in 450 ml distilled $H_2O$. Because of the limited solubility of $(NH_4)_2TiF_6$ the salt was added to the slurry as crystals. The weight of added $(NH_4)_2TiF_6$ was 7.83 grams and was an amount sufficient to replace 75% of the framework aluminum with titanium. The reaction mixture was then digested at reflux for 30 minutes, filtered and washed with warm distilled water until testing of the wash water was negative for both aluminum and fluoride ions. The chemical analyses for the starting mordenite and the molecular sieve product (referred to herein as LZ-227) are set forth in Table 5 wherein this LZ-227 product is designated Product C. A comparison of the properties of the LZ-227 product (Product C) with the starting mordenite is shown in Table 6. The framework mole fraction of tetrahedra are set forth below for the starting mordenite and Product C:

(a) Mole fraction of Oxides ($TO_2$):
Starting Mordenite: $(Al_{0.106}Si_{0.740}\square_{0.154})O_2$
LZ-227 Product C: $(Al_{0.072}Si_{0.776}Ti_{0.024}\square_{0.128})O_2$
(b) Mole fraction of aluminum removed, N: 0.034
(c) Percent aluminum removal, N/a×100: 32
(d) Change in Defect Structure Factor, $\Delta z$: −0.026
(e) Moles of titanium substitute per mole of aluminum removed: 0.71

TABLE 5

| | Starting Mordenite | LZ-227 (Product A) | LZ-227 (Product B) | LZ-227 (Product C) |
|---|---|---|---|---|
| $Na_2O$, wt. % | 0.19 | — | — | — |
| $(NH_4)_2O$, wt. % | — | 2.38 | 3.07 | 3.01 |
| $Fe_2O_3$, wt. % | 0.17 | 0.16 | — | — |
| $TiO_2$, wt. % | 0.97 | 4.65 | 3.52 | 3.46 |
| $Al_2O_3$, wt. % | 10.75 | 6.35 | 6.70 | 6.70 |
| $SiO_2$, wt. % | 88.77 | 83.79 | 86.25 | 85.16 |
| $F_2$, wt. % | — | 0.16 | 0.16 | 0.13 |
| $Na^+/Al$ | 0.03 | — | — | — |
| $NH_4^+/Al$ | — | 0.74 | 0.90 | 0.88 |
| Cation Equivalent $M^+/Al$ | 0.03 | 0.74 | 0.90 | 0.88 |
| $SiO_2/Al_2O_3$ | 14.00 | 22.38 | 21.81 | 21.57 |
| $Si/(Al_2 + Ti_2)$ | 14.00 | 15.26 | 16.34 | 16.22 |

TABLE 6

| | Starting Mordentie | LZ-227 (Product A) | LZ-227 (Product B) | LZ-227 (Product C) |
|---|---|---|---|---|
| X-Ray Crystallinity | | | | |
| % by Peak Intensity | 100 | 87 | 109 | 106 |
| % by Peak Area | 100 | 82 | 109 | 108 |
| Crystal Collapse Temp; °C. (DTA) | 1010 | 1050 | 1022 | 1028 |
| | | 1125 | 1140 | 1140 |
| Framework Infrared: | | | | |
| Asymmetric Stretch, | | | | |

TABLE 6-continued

|  | Starting Mordentie | LZ-227 (Product A) | LZ-227 (Product B) | LZ-227 (Product C) |
|---|---|---|---|---|
| $cm^{-1}$ | 1073 | 1079 | 1075 | 1073 |
| Symmetric Stretch, $cm^{-1}$ | 801 | 811 | 805 | 809 |
| Hydroxyl Infrared: | | | | |
| Absolute Absorbance at 3710 $cm^{-1}$ | 0.364 | 0.212 | 0.378 | 0.303 |
| Defect Structure Factor, z | 0.154 | 0.090 | 0.160 | 0.128 |
| McBain Adsorption: | | | | |
| Wt. % $O_2$ 100 torr, $-183°$ C. | 19.1 | 18.8 | 18.4 | 16.6 |
| Wt. % $H_2O$, 4.6 torr, 25°C. | 16.2 | 13.3 | 16.6 | 17.4 |

(4) The molecular sieves denominated herein as "LZ-227" have the characteristic crystal structure of mordenite as indicated by an x-ray diffraction having at least the d-spacings set forth in Table C, hereinafter, and having titanium atoms in the crystal lattice in the form of $TiO_4$ tetrahedra, preferably in an amount of at least 1.0 per 10,000Å$^3$:

TABLE C

| d(Å) | Relative Intensity |
|---|---|
| 13.5 ± 0.2 | m |
| 9.0 ± 0.2 | s |
| 6.5 ± 0.1 | m |
| 4.5 ± 0.1 | m |
| 3.8 ± 0.1 | m |
| 3.5 ± 0.1 | s |
| 3.4 ± 0.1 | s |
| 3.2 ± 0.1 | m |

(5) The x-ray powder pattern of LZ-227 Product A contained in extraneous peak which was identified as $Al(OH)_3$ (gibbsite). The x-ray powder patterns of Products B and C did not contain any extraneous peaks and there was no observable increase in background due to the presence of amorphous materials. Maintenance of both oxygen and water capacities demonstrates the products are highly crystalline. The properties of the LZ-227 products indicate that the products contain titanium incorporated into the zeolite framework.

EXAMPLE 4

(1) Twenty-five grams of a hydronium-exchanged synthetic mordenite (ZEOLON (TM), a trademark of Norton Co.), containing 52.8 millimoles of aluminum as $Al_2O_3$, were slurried in 450 ml distilled $H_2O$. Because of the limited solubility of $(NH_4)_3FeF_6$, the salt was added to the slurry as crystals. The weight of added $(NH_4)_3FeF_6$ was 2.95 grams and was an amount sufficient to replace 25% of the framework aluminum with iron. The reaction mixture was digested at reflux under a $N_2$ atmosphere for 48 hours, filtered and washed with warm distilled water until testing of the wash water was negative for both aluminum and fluoride ions. The chemical analyses for the starting mordenite and the molecular sieve product zeolite (referred to herein as "LZ-226") are set forth in Table 7 wherein this LZ-226 product is designated Product A. A comparison of the properties of Product A with the starting mordenite is shown in Table 8. The framework mole fractions of tetrahedra are set forth below for the starting mordenite and Product A:

(a) Mole fraction of Oxides ($TO_2$):
   Starting mordenite: $(Al_{0.106}Si_{0.740}\square_{0.154})O_2$
   LZ-226 Product A: $(Al_{0.080}Si_{0.816}Fe_{0.038}\square_{0.066})O_2$
(b) Mole fraction of aluminum removed, N; 0.026
(c) Percent aluminum removal, N/a×100:25
(d) Change in Defect Structure Factor, $\Delta z$: $-0.088$
(e) Moles of iron substituted per mole of aluminum removed: 1.46

(2) Twenty-five grams of a hydronium-exchanged synthetic mordenite (ZEOLON (½), a trademark of Norton Co.), containing 52.8 millimoles of aluminum as $Al_2O_3$ were slurried in 450 ml distilled $H_2O$. Because of the limited solubility of $Na_3FeF_6$, the salt was added as crystals. The weight of added $Na_3FeF_6$ was 5.91 grams and was an amount sufficient to replace 50% of the framework aluminum with iron. The reaction mixture was digested at reflux for 30 minutes under an atmosphere of $N_2$, filtered and washed with warm distilled water until testing of the wash water was negative for both aluminum and fluoride ions. The chemical analyses for the starting mordenite and the molecular sieve product (referred to herein as LZ-226) are shown in Table 7 wherein this LZ-226 product is designated Product B. A comparison of the properties of product B with the starting mordenite is set forth in Table 8. The framework mole fractions of tetrahedra are set forth below for the starting mordenite and the LZ-226 product B:

(a) Mole fractions of oxides, ($TO_2$):
   Starting H Mordenite: $(Al_{0.106}Si_{0.740}\square_{0.154})O_2$
   LZ-226, Product B: $(Al_{0.072}Si_{0.761}Fe_{0.035}\square_{0.132})O_2$
(b) Mole fraction of aluminum removed, N: 0.034
(c) Percent aluminum removed, N/a×100: 32
(d) Change in Defect Structure Factor, $\Gamma z$: $-0.022$
(e) Moles of Iron substituted per mole of aluminum removed: 1.03

(3) Twenty-five grams of a hydronium-exchanged synthetic mordenite (ZEOLON (½), a trademark of Norton Co.), containing 52.8 millimoles of aluminum as $Al_2O_3$, were slurried in 450 ml distilled $H_2O$. Because of the limited solubility of $Na_3FeF_6$, the salt was added to the slurry as crystals. The weight of added salt was 8.86 grams was an amount sufficient to replace 75% of the framework aluminum with iron. The reaction mixture was digested at reflux for 30 minutes under an atmosphere of $N_2$, filtered and washed with warm distilled water until testing of the wash water was negative for both aluminum and fluoride ions. The chemical analyses for the starting mordenite and the molecular sieve product zeolite (referred to herein as LZ-226) are set forth in Table 7 wherein this LZ-226 product is designated Product C. A comparison of the properties of this LZ-226 product (Product C) with the starting mordenite is shown in Table 8. The framework mole fractions of tetrahedra are set forth below for the starting mordenite and this LZ-226 product.

(a) Mole fractions of Oxides, ($TO_2$):
   Starting mordenite: $(Al_{0.106}Si_{0.740}\square_{0.154})O_2$
   LZ-226, Product C: $(Al_{0.060}Si_{0.705}Fe_{0.049}\square_{0.187})O_2$
(b) Mole fraction of aluminum removed, N: 0.046
(c) Percent aluminum removed, N/a×100: 43
(d) Change in Defect Structure Factor, $\Delta z$: 0.033
(e) Moles of iron substituted per mole of aluminum removed: 1.07

TABLE 7

|  | Starting Mordenite | LZ-226 (Product A) | LZ-226 (Product B) | LZ-226 (Product C) |
|---|---|---|---|---|
| Na$_2$O, wt. % | 0.19 | — | 2.81 | 2.80 |
| (NH$_4$)$_2$O, wt. % | — | 2.94 | 0.08 | 0.06 |
| Fe$_2$O$_3$, wt. % | 0.17 | 4.08 | 5.15 | 5.95 |
| TiO$_2$, wt. % | 0.97 | 0.46 | — | — |
| Al$_2$O$_3$, wt. % | 10.75 | 8.04 | 6.79 | 7.70 |
| SiO$_2$, wt. % | 88.77 | 87.20 | 84.92 | 83.38 |
| F$_2$, wt. % | — | 0.46 | 0.36 | 0.68 |
| Na$^+$/Al | 0.03 | — | 0.68 | 0.77 |
| NH$_4^+$/Al | — | 0.72 | 0.02 | 0.02 |
| Cation Equivalent M$^+$/Al | 10.03 | 0.72 | 0.71 | 0.79 |
| SiO$_2$/Al$_2$O$_3$ | 14.00 | 18.39 | 21.22 | 23.79 |
| Si/(Al$_2$ + Fe$_2$) | 14.00 | 13.90 | 14.29 | 13.03 |

TABLE 8

|  | Starting Mordenite | LZ-226 (Product A) | LZ-226 (Product B) | LZ-226 (Product C) |
|---|---|---|---|---|
| X-Ray Crystallinity: | | | | |
| % by Peak Intensity | 100 | 80 | 65* | 56* |
| % by Peak Area | 100 | 74 | 61 | 54 |
| Crystal Collapse Temp., °C.(DTA) | 1010 | 992, 1105 | 926 | 900** |
| Framework Infrared: | | | | |
| Asymmetric Stretch, cm$^{-1}$ | 1073 | 1072 | 1070 | 1078 |
| Symmetric Stretch, cm$^{-1}$ | 801 | 811 | 809 | 808 |
| Hydroxyl Infrared: | | | | |
| Absolute Absorbance at 3710 cm$^{-1}$ | 0.364 | 0.155 | 0.312 | 0.440 |
| Defect Structure Factor, z | 0.154 | 0.066 | 0.132 | 0.187 |
| McBain Adsorption: | | | | |
| Wt. % O$_2$, 100 torr, −183° C. | 19.1 | 19.0 | 17.7 | 17.4 |
| Wt. % H$_2$O, 4.6 torr, 25° C. | 16.2 | 13.4 | 15.9 | 15.6 |

*The x-ray powder pattern also showed the presence of —FeOOH, —Iron oxyhydroxide.
**approximately 900° C. ± 10° C.

The molecular sieves denominated herein as "LZ-226" have the characteristic crystal structure of mordenite as indicated by an x-ray diffraction pattern having at least the d-spacings set forth in Table D, below, and having iron atoms in the crystal lattice in the form of "FeO$_4$" tetrahedra preferably in an amount of at least 1.0 per 10,000Å$^3$.

TABLE D

| d(Å) | Relative Intensity |
|---|---|
| 13.5 ± 0.2 | m |
| 9.0 ± 0.2 | s |
| 6.5 ± 0.1 | m |
| 4.5 ± 0.1 | s |
| 4.0 ± 0.1 | m |
| 3.8 ± 0.1 | m |
| 3.5 ± 0.1 | s |
| 3.4 ± 0.1 | s |
| 3.2 ± 0.1 | m |

(4) The x-ray powder patterns of the LZ-226, particularly those of Product B and C, contained several small peaks which were identified as trace quantities of β-iron oxyhydroxide (β-FeOOH). These two products were prepared using the sodium salt of the iron fluoride.

EXAMPLE 5

(1) Seventy grams of an ammonium-exchanged zeolite L, containing 272.0 millimoles of aluminum as Al$_2$O$_3$, were slurried in 500 ml distilled H$_2$O. Because of the limited solubility of (NH$_4$)$_2$TiF$_6$, the salt was added to the slurry as crystals. The weight of added (NH$_4$)$_2$TiF$_6$ was 26.66 grams and was an amount sufficient to replace 50% of the framework aluminum with titanium. Following the addition of the (NH$_4$)$_2$TiF$_6$ crystals the reaction mixture was digested at reflux for 17 hours, filtered and washed with warm distilled water until testing of the wash water was negative for both aluminum and fluoride ions. The chemical analyses for the staring zeolite L and the molecular sieve product (referred to herein as "LZ-229") are set in Table 9 wherein this LZ-229 product is designated Product A. A comparison of the properties of this LZ-229 product (Product A) with the starting zeolite L is shown in Table 10. The framework mole fractions of tetrhedra are set forth below for the starting zeolite L and this LZ-229 product.

(a) Mole fractions of oxides, (TO$_2$):
  Starting Zeolite NH$_4$L: (Al$_{0.250}$Si$_{0.725}$□$_{0.025}$)O$_2$
  LZ-229, Product A: (Al$_{0.136}$Si$_{0.693}$Ti$_{0.095}$□$_{0.076}$)O$_2$
(b) Mole fraction of aluminum removed, N: 0.136
(c) Percent aluminum removed, N/a×100: 46
(d) Change in Defect Structure Factor, Δz: 0.051
(e) Moles of titanium substituted per mole of aluminum removed: 0.83

(2) Twenty grams of an ammonium-exchanged zeolite L, containing 77.7 millimoles of aluminum as Al$_2$O$_3$ were slurried in 250 ml distilled H$_2$O. Because of the limited solubility of (NH$_4$)$_2$TiF$_6$, the salt was added to the slurry as crystals. The weight of added (NH$_4$)$_2$TiF$_6$ was 7.62 grams and was an amount sufficient to replace 50% of the framework aluminum with titanium. Following the addition of the (NH$_4$)$_2$TiF$_6$ crystals the reaction mixture was digested at reflux for 30 minutes, filtered and washed with warm distilled water until testing of the wash water was negative for both aluminum and fluoride ions. The chemical analyses for the starting zeolite L and the molecular sieve product (referred to herein as "LZ-229") are set forth in Table 9 wherein this LZ-229 product is designated as Product B. A comparison of the properties of this LZ-229 product (Product B) with the starting zeolite L is shown in Table 10. The framework mole fractions of tetrahedra are set forth below for the starting zeolite L and this LZ-229 product:

(a) Mole fractions of Oxides, (TO$_2$):
  Starting zeolite NH$_4$L (Al$_{0.250}$Si$_{0.725}$□$_{0.025}$)O$_2$
  LZ-229, Product B: (Al$_{0.205}$Si$_{0.712}$Ti$_{0.028}$□$_{0.055}$)O$_2$
(b) Mole fraction of aluminum removed, N: 0.045
(c) Percent aluminum removed, N/a×100: 18
(d) Change in Defect Structure Factor, Δz: 0.030
(e) Moles of titanium substituted per mole of aluminum removed: 0.62

(3) Twenty grams of an ammonium-exchanged zeolite L, containing 77.7 millimoles of aluminum as Al$_2$O$_3$ were slurried in 250 ml distilled H$_2$O. Because of the limited solubility of (NH$_4$)$_2$TiF$_6$, the salt was added to the slurry as crystals. The weight of added (NH$_4$)$_2$TiF$_6$ was 11.43 grams and was an amount sufficient to replace 75% of the framework aluminum with titanium. The reaction mixture was digested at reflux for 30 minutes, filtered and washed with warm distilled water until testing of the wash water was negative for both aluminum and fluoride ions. The chemical analyses for the starting zeolite L and the molecular sieve product (referred to herein as LZ-229) are set forth in Table 9 wherein this LZ-229 product is designated Product C.

A comparison of the properties of this LZ-229 product (Product C) with the starting zeolite L is shown in Table 10.

The framework mole fractions of tetrahedra are set forth below for the starting zeolite L and this LZ-229 product
(a) Mole fractions of Oxides, (TO$_2$):
Starting NH$_4$L: (Al$_{0.250}$Si$_{0.725}$□$_{0.025}$)O$_2$
LZ-229, Product C (Al$_{0.187}$Si$_{0.688}$Ti$_{0.054}$□$_{0.071}$)O$_2$
(b) Mole fraction of aluminum removed, N: 0.03
(c) Percent aluminum removed, N/a×100: 25
(d) Change in Defect Structure Factor, Δz: 0.046
(e) Moles of Titanium substituted per mole of aluminum removed: 0.86

TABLE 9

|  | Starting zeolite L | LZ-229 (Product A) | LZ-229 (Product B) | LZ-229 (Product C) |
|---|---|---|---|---|
| Na$_2$O, wt. % | — | — | 0.08 | — |
| (NH$_4$)$_2$O, wt. % | 7.88 | 4.67 | 6.94 | 6.83 |
| K$_2$O, wt. % | 2.20 | 1.59 | 1.97 | 1.94 |
| TiO$_2$, wt. % | — | 12.64 | 3.54 | 7.17 |
| Al$_2$O$_3$, wt. % | 19.81 | 11.85 | 16.88 | 15.72 |
| Si$_2$O, wt. % | 67.76 | 69.25 | 68.90 | 68.34 |
| F$_2$, wt. % | — | 0.42 | 0.13 | 0.24 |
| Na$^+$/Al | — | — | 0.01 | — |
| NH$_4^+$/Al | 0.78 | 0.77 | 0.81 | 0.85 |
| K$^+$/Al | 0.12 | 0.15 | 0.13 | 0.13 |
| Cation Equivalent, M$^+$/Al | 0.90 | 0.92 | 0.94 | 0.98 |
| SiO$_2$/Al$_2$O$_3$ | 5.80 | 9.92 | 6.93 | 7.37 |
| Si/(Al$_2$ + Ti$_2$) | 5.80 | 6.01 | 6.11 | 5.71 |

TABLE 10

|  | Starting zeolite L | LZ-229 (Product A) | LZ-229 (Product B) | LZ-229 (Product C) |
|---|---|---|---|---|
| X-Ray Crystallinity: | | | | |
| % by Peak Intensity | 100 | 44 | 73 | 73 |
| % by Peak Area | 100 | 44 | 74 | 74 |
| Crystal Collapse Temp., °C.(DTA) | 870, 1132 | 900 | 870, 972, 1132 | 870, 1000, 1145 |
| Framework Infrared: | | | | |
| Asymmetric Stretch, cm$^{-1}$ | 1100, 1031 | 1111, 1035 | 1100, 1062, 1032 | 1104, 1064, 1033 |
| Symmetric Stretch, cm$^{-1}$ | 770, 726 | 777, 725 | 773, 732 | 774, 727 |
| Hydroxyl Infrared: | | | | |
| Absolute Absorbance at 3710 cm$^{-1}$ | 0.058 | 0.180 | 0.130 | 0.167 |
| Defect Structure Factor, z | 0.025 | 0.076 | 0.055 | 0.071 |
| McBain Adsorption: | | | | |
| Wt. % O$_2$, −183° C., 100 torr, | 16.46 | 11.19 | 15.54 | 15.78 |
| Wt. % H$_2$O, 4.6 torr, 25° C. | 19.05 | 13.52 | 18.83 | 19.55 |

(4) The molecular sieves denominated herein as "LZ-229" have the characteristic crystal structure of zeolite L as indicated by an x-ray diffraction pattern having at least the d-spacings set forth in Table E, below, and having titanium atoms in the crystal lattice in the form of TiO$_4$ tetrahedra, preferably in an amount of at least 1.0 per 10,000Å$^3$:

TABLE E

| d(Å) | Relative Intensity |
|---|---|
| 15.8 ± 0.2 | s |
| 6.0 ± 0.1 | m |
| 5.8 ± 0.1 | mw |
| 4.6 ± 0.1 | m |
| 4.4 ± 0.1 | mw |
| 4.3 ± 0.1 | mw |
| 3.9 ± 0.1 | m |
| 3.66 ± 0.1 | m |
| 3.48 ± 0.1 | m |
| 3.28 ± 0.1 | mw |
| 3.18 ± 0.1 | m |
| 3.07 ± 0.1 | m |
| 2.91 ± 0.1 | m |

EXAMPLE 6

(1) Seventy grams of an ammonium-exchanged zeolite L containing 272.0 millimoles of aluminum, as Al$_2$O$_3$, were slurried in 500 ml distilled H$_2$O. Because of the limited solubility of (NH$_4$)$_3$FeF$_6$, the salt was added to the slurry as crystals. The weight of added (NH$_4$)$_3$FeF$_6$ was 30.16 grams and was an amount sufficient to replace 50% of the zeolitic aluminum with iron. The reaction mixture was then digested at reflux for 2 hours, under an atmosphere of N$_2$, filtered and washed with warm distilled water until testing of the wash water was negative for both aluminum and fluoride ions. The chemical analyses for the starting zeolite L and the moleculer sieve product (referred to herein as "LZ-228") are set forth in Table 11 wherein this LZ-228 product is designated Product A. A comparison of the properties of this LZ-228 product (Product A) with the starting zeolite L is shown in Table 12.

The framework mole fractions of tetrahedra are set forth below for the starting zeolite L and this LZ-228 product:
(a) Mole fractions of Oxides, (TO$_2$):
Starting zeolite NH$_4$L: (Al$_{0.250}$Si$_{0.725}$□$_{0.025}$)O$_2$
LZ-228, Product A: (Al$_{0.172}$Si$_{0.664}$Fe$_{0.109}$□$_{0.055}$)O$_2$
(b) Mole fraction of Aluminum Removed, N: 0.078
(c) Percent aluminum removed, N/a×100: 31
(d) Change in Defect Structure Factor Δz: 0.030
(e) Moles of Iron substituted per mole of aluminum removed: 1.40

(2) Twenty grams of an ammonium-exchanged zeolite L, containing 77.7 millimoles of aluminum, as Al$_2$O$_3$, were slurried in 250 ml distilled H$_2$O. Because of the limited solubility of (NH$_4$)$_3$FeF$_6$, the salt was added to the slurry as crystals. The weight of added (NH$_4$)$_3$FeF$_6$ was 8.62 grams and was an amount sufficient to replace 50% of the zeolite aluminum with iron. The reaction mixture was then digested at reflux for 30 minutes under an atmosphere of N$_2$, filtered and washed with warm distilled water until testing of the wash water was negative for both aluminum and fluoride ions. The chemical analyses for the starting zeolite NH₄L and the molecular sieve product (referred to herein as "LZ-228") are set forth in Table 11 wherein this LZ228 product is designated Product B. A comparison of the properties of this LZ-228 product (Product B) with the starting zeolite L is shown in Table 12.

The framework mole fractions of the tetrahedra are set forth below for the starting zeolite L and this LZ-228 product:

(a) Mole fractions of Oxides, (TO$_2$):
Starting zeolite NH₄L: $(Al_{0.250}Si_{0.725}\square_{0.025})O_2$ LZ-228, Product B: $(Al_{0.173}Si_{0.652}Fe_{0.117}\square_{0.058})O_2$ (b) Mole fraction of Aluminum Removed, N: 0.077

(c) Percent aluminum removed N/A×100: 31

(d) Change in Defect Structure Factor Δz: 0.035

(e) Moles of Iron substituted per mole of aluminum removed: 1.52

(3) Twenty grams of an ammonium-exchanged zeolite L containing 77.7 millimoles of aluminum, as Al₂O₃, were slurried in 250 ml distilled H₂O. Because of the limited solubility of (NH₄)₃FeF₆, the salt was added to the slurry as crystals. The weight of added (NH₄)₃FeF₆ was 12.93 grams and was an amount sufficient to replace 75% of the zeolite aluminum with iron. The reaction mixture was then digested at reflux for 30 minutes under a protective atmosphere of N₂, filtered and washed with warm distilled water until testing of the wash water was negative for both aluminum and fluoride ions. The chemical analyses for the starting zeolite L and the LZ-228 product (designated Product C) are set forth in Table 11. A comparison of the properties of this LZ-228 product (Product C) with the starting zeolite L is shown in Table 12.

The framework mole fractions of tetrahedra are set forth below for the starting zeolite L and this LZ-228 product:

(a) Mole fractions of Oxides, (TO$_2$):
Starting zeolite NH₄L: $(Al_{0.250}Si_{0.725}\square_{0.025})O_2$
LZ-228, Product C: $(Al_{0.156}Si_{0.616}Fe_{0.098}\square_{0.130})O_2$ (b) Mole fraction of aluminum removed, N: 0.094

(c) Percent aluminum removed, N/A×100: 38

(d) Change in Defect Structure Factor Δz: 0.105

(e) Moles of iron substituted per mole of aluminum removed: 0.104

TABLE 11

|  | Starting Zeolite L | LZ-228 (Product A) | LZ-228 (Product B) | LZ-228 (Product C) |
|---|---|---|---|---|
| Na₂O, wt % | — | — | — | 0.79 |
| (NH₄)₂O, wt % | 7.88 | 5.63 | 5.85 | 5.17 |
| K₂O, wt % | 2.20 | 1.72 | 1.64 | 1.88 |
| Fe₂O₃, wt % | — | 13.91 | 15.10 | 13.51 |
| Al₂O₃, wt % | 19.81 | 14.02 | 15.11 | 13.63 |
| SiO₂, wt % | 67.76 | 63.79 | 63.58 | 63.57 |
| F₂, wt % | — | 1.05 | 0.91 | 0.93 |
| NH₄⁺/Al | 0.78 | 0.79 | 0.80 | 0.74 |
| K⁺/Al | 0.12 | 0.13 | 0.12 | 0.15 |
| Cation Equivalent, M⁺/Al | 0.90 | 0.92 | 0.93 | 0.99 |
| SiO₂/Al₂O₃ | 5.80 | 7.72 | 7.55 | 7.91 |
| Si/(Al₂ + Fe₂) | 5.80 | 4.73 | 4.51 | 4.85 |

TABLE 12

|  | Starting Zeolite L | LZ-228 (Product A) | LZ-228 (Product B) | LZ-228 (Product C) |
|---|---|---|---|---|
| X-Ray Crystallinity: | | | | |
| % by Peak Intensity | 100 | 33 | 46 | 46 |
| % by Peak Area | 100 | 35 | 46 | 48 |
| Crystal Collapse Temp., °C. (DTA) | 870, 1132 | 840 | 845 | 855 |
| Framework Infrared: | | | | |
| Asymmetric Stretch, cm⁻¹ | 1100, 1031 | 1105, 1062, 1033 | 1105, 1064, 1042 | 1099, 1065, 1031 |
| Symmetric Stretch, cm⁻¹ | 770, 726 | 776, 724 | 774, 723 | 772, 724 |
| Hydroxyl Infrared: | | | | |
| Absolute Absorbance 3710 cm⁻¹ | 0.058 | 0.130 | 0.138 | 0.307 |
| Defect Structure Factor, z | 0.025 | 0.055 | 0.058 | 0.130 |
| McBain Adsorption: | | | | |
| wt. % O₂, −183° C., 100 torr | 16.46 | 13.57 | 13.38 | 16.76 |
| wt. % H₂O, 4.6 torr, 25° C. | 19.05 | 15.32 | 17.19 | 20.30 |

(4) The molecular sieves denominated herein as "LZ-228" have the characteristic crystal structure of zeolite L as indicated by an x-ray powder diffraction pattern having at least the d-spacings set forth in Table F, below, and having iron atoms in the crystal lattice in the form of FeO₄ tetrahedra, preferably in an amount of at least 1.0 per 10,000Å³.

TABLE F

| d(Å) | Relative Intensity |
|---|---|
| 15.8 ± 0.2 | s |
| 6.0 ± 0.1 | m |
| 5.8 ± 0.1 | mw |
| 4.6 ± 0.1 | m |
| 4.4 ± 0.1 | mw |
| 4.3 ± 0.1 | mw |
| 3.9 ± 0.1 | m |
| 3.66 ± 0.1 | m |
| 3.48 ± 0.1 | m |
| 3.28 ± 0.1 | mw |
| 3.18 ± 0.1 | m |
| 3.07 ± 0.1 | mw |
| 2.91 ± 0.1 | m |

(5) Fluoresence by the heavier iron atoms would account for the reduced x-ray crystallinity. A probative measure of the retained crystallinity and void volume of iron-containing product is available from the H₂O and O₂ adsorption capacities which indicate that the products were highly crystalline. All properties taken together indicate that iron has been incorporated into the framework of the zeolite L as both cation and tetrahedral atom.

EXAMPLE 7

1. Ten grams of an ammonium-exchanged, natural mineral clinoptilolite, containing 25.1 millimoles of aluminum as $Al_2O_3$, were slurried in 250 ml distilled $H_2O$. Because of the limited solubility of $(NH_4)_2TiF_6$, the salt was added to the slurry as crystals. The weight of added $(NH_4)_2TiF_6$ was 2.49 grams and was an amount sufficient to replace 50% of the framework aluminum of the zeolite with titanium. The reaction mixture was refluxed for 30 minutes, filtered and washed with warm distilled water until testing of the wash water was negative for both aluminum and fluoride ions. The chemical analyses for the starting clinoptilolite and the molecular sieve product (referred to herein as LZ-231) are set forth in Table 13.

TABLE 13

|  | Starting Clinoptilolite | LZ-231 Product |
|---|---|---|
| $Na_2O$, wt %: | 0.55 | 0.45 |
| $(NH_4)_2O$, wt %: | 5.19 | 4.84 |
| $K_2O$, wt %: | 0.77 | 0.54 |
| $TiO_2$, wt %: | — | 3.08 |
| $Al_2O_3$, wt %: | 12.82 | 12.10 |
| $SiO_2$, wt. %: | 77.90 | 75.69 |
| $F_2$, wt %: | — | 0.19 |
| $Na^+/Al$: | 0.07 | 0.06 |
| $NH_4^+/Al$: | 0.79 | 0.78 |
| $K^+/Al$: | 0.07 | 0.05 |
| Cation Equivalent, $M^+/Al$: | 0.93 | 0.89 |
| $SiO_2/Al_2O_3$: | 10.31 | 10.61 |
| $Si/(Al_2 + Ti_2)$: | 10.31 | 9.13 |

A comparison of the properties of the LZ-231 product with the starting clinoptilolite is shown in Table 14:

TABLE 14

|  | Starting Clinoptilolite | LZ-231 Product |
|---|---|---|
| X-Ray Crystallinity: |  |  |
| % by Peak Instensity: | 100 | 75 |
| % by Peak Area: | 100 | 75 |
| Crystal Collapse Temp., °C. (DTA): | 528 | None Observed |
| Framework Infrared: |  |  |
| Asymmetric Stretch, $cm^{-1}$: | 1082 | 1065 |
| Symmetric Stretch, $cm^{-1}$: | 795,778 | 797,778 |
| Hydroxyl Infrared: |  |  |
| Absolute Absorbance 3710 $cm^{-1}$: | 0.055 | 0.080 |
| Defect Structure Factor, z: | 0.023 | 0.034 |
| McBain Adsorption: |  |  |
| wt % $O_2$, 100 torr. −183° C.: | 15.10 | 15.26 |
| wt % $H_2O$, 4.6 torr, 25° C.: | 11.66 | 14.80 |

The framework mole fractions of tetrahedra are set forth below for the starting $NH_4$ clinoptilolite and the LZ-231 product:

(a) Mole fractions of oxides ($TO_2$):
Starting $NH_4$ clinoptilolite: $(Al_{0.159}Si_{0.818}\square_{0.023})O_2$
LZ-231 product: $(Al_{0.150}Si_{0.792}Ti_{0.024}\square_{0.034})O_2$
(b) Mole fraction of aluminum removed, N; 0.009
(c) Percent aluminum removed, $N/a \times 100$: 6
(d) Change in Defect Factor, $\Delta z$: 0.011
(e) Moles of titanium substituted per mole of aluminum removed: 2.67

(2) The molecular sieves denominated herein as "LZ-231" have the characteristic crystal structure of zeolite clinoptilolite as indicated by an x-ray powder diffraction pattern having at least the d-spacings set forth in Table G below and having titanium atoms in the crystal lattice in the form of $TiO_4$ tetrahedra, preferably in an amount of at least 1.0 per 10,000$Å^3$.

TABLE G

| d,(Å) | Relative Intensity |
|---|---|
| 8.9 ± 0.2 | vs |
| 7.8 ± 0.2 | m |
| 6.7 ± 0.2 | mw |
| 6.6 ± 0.2 | mw |
| 5.1 ± 0.2 | mw |
| 3.95 ± 0.1 | ms |
| 3.89 ± 0.1 | m |
| 3.41 ± 0.1 | m |
| 3.37 ± 0.1 | mw |
| 3.33 ± 0.1 | m |
| 3.17 ± 0.1 | mw |

(3) When all of the properties of the LZ-231 of this example are considered, it was concluded that the 3.08 wt. % $TiO_2$ indicates that titanium was incorporated into the framework of the clinoptilolite.

EXAMPLE 8

(1) Ten grams of an ammonium-exchanged synthetic TMA offretite containing 27.6 millimoles of aluminum as $Al_2O_3$, were slurried in 250 ml distilled $H_2O$. Because of the limited solubility of $(NH_4)_2TiF_6$, the salt was added to the slurry as crystals. The weight of added $(NH_4)_2TiF_6$, was 2.73 grams and was an amount sufficient to replace 50% of the aluminum of the zeolite with titanium. The reaction mixture was refluxed for 30 minutes, filtered and washed with warm distilled water until testing of the wash water was negative for both aluminum and fluoride ions. The chemical analyses for the starting offretite and the product (referred to herein as "LZ-233") are set forth in Table 15:

TABLE 15

|  | Starting Offretite | LZ-233 Product |
|---|---|---|
| $Na_2O$, wt % | — | — |
| $(NH_4)_2O$, wt % | 5.31 | 5.02 |
| $K_2O$, wt % | 2.48 | 2.10 |
| $TiO_2$, wt % | — | 2.80 |
| $Al_2O_3$, wt % | 14.05 | 12.72 |
| $SiO_2$, wt. % | 76.15 | 76.90 |
| $F_2$, wt % | — | 0.11 |
| $Na^+/Al$ | — | — |
| $NH_4^+/Al$ | 0.74 | 0.77 |
| $K^+/Al$ | 0.19 | 0.18 |
| Cation Equivalent, $M^+/Al$ | 0.93 | 0.95 |
| $SiO_2/Al_2O_3$ | 9.20 | 10.26 |
| $Si/(Al_2 + Ti_2)$ | 9.20 | 9.00 |

A comparison of the properties of the LZ-233 product with the starting offretite is shown in Table 16:

TABLE 16

|  | Starting Offretite | LZ-233 Product |
|---|---|---|
| X-Ray Crystallinity: |  |  |
| % by Peak Instensity: | 100 | 85 |
| % by Peak Area: | 100 | 87 |
| Crystal Collapse | 1001 | 1010 |

TABLE 16-continued

| | Starting Offretite | LZ-233 Product |
|---|---|---|
| Temp., °C. (DTA): | | |
| Framework Infrared: | | |
| Asymmetric Stretch cm$^{-1}$: | 1083 | 1085 |
| Symmetric Stretch, cm$^{-1}$: | 789 | 791 |
| Hydroxyl Infrared: | | |
| Absolute Absorbance 3710 cm$^{-1}$: | 0.140 | 0.116 |
| Defect Structure Factor, z: | 0.059 | 0.049 |
| McBain Adsorption: | | |
| wt % O$_2$, 100 torr. −183° C.: | 25.33 | 24.60 |
| wt % H$_2$O, 4.6 torr, 25° C.: | 21.10 | 23.94 |

The framework mole fractions of tetrahedra are set forth below for the starting offretite and the LZ-233 product:

(a) Mole fractions of oxides (TO$_2$):
  Starting NH$_4$ Offretite: (Al$_{0.168}$Si$_{0.773}$☐$_{0.059}$)O$_2$
  LZ-233 product: (Al$_{0.152}$Si$_{0.778}$Ti$_{0.021}$☐$_{0.049}$)O$_2$
(b) Mole fraction of aluminum removed, N; 0.016
(c) Percent aluminum removed, N/a=100: 10
(d) Change in Defect Structure Factor, Δz: −0.010
(e) Moles of titanium substituted per mole of aluminum removed: 1.31

(2) The molecular sieves denominated herein as "LZ-233" have the characteristic crystal structure of zeolite offretite as indicated by an x-Ray powder diffraction pattern having at least the d-spacings set forth in Table H below and having titanium atoms in the crystal lattice in the form of TiO$_4$ tetrahedra, preferably in an amount of at least 1.0 per 10,000 Å$^3$.

TABLE H

| d,(Å) | Relative Intensity |
|---|---|
| 11.4 ± 0.2 | vs |
| 6.6 ± 0.1 | ms |
| 5.7 ± 0.1 | mw |
| 4.31 ± 0.1 | m |
| 3.75 ± 0.1 | m |
| 3.58 ± 0.1 | m |
| 3.29 ± 0.1 | mw |
| 3.14 ± 0.1 | mw |
| 2.84 ± 0.1 | m |
| 2.67 ± 0.1 | mw |

(3) When all the aforementioned properties are considered together such are consistent with the conclusion that the 2.80 wt % TiO$_2$ found in the LZ-233 product represents titanium incorporated into the framework of the offretite.

EXAMPLE 9

(1) Ten grams of an ammonium-exchanged, natural mineral erionite containing 33.0 millimoles of aluminum, as Al$_2$O$_3$, were slurried in 250 ml distilled H$_2$O. Because of the limited solubility of (NH$_4$)$_2$TiF$_6$, the salt was added to the slurry as crystals. The weight of added (NH$_4$)$_2$TiF$_6$ was 3.26 grams and was an amount sufficient to replace 50% of the aluminum of the zeolites with titanium. The reaction mixture was refluxed for 30 minutes, filtered and washed with warm distilled water until tests of the wash water were negative for both aluminum and fluoride ions. The chemical analyses for the starting NH$_4$ erionite and the molecular sieve product (referred to herein as "LZ-232") are set forth in Table 17:

TABLE 17

| | Starting Erionite | LZ-232 Product |
|---|---|---|
| Na$_2$O, wt % | 0.35 | 0.23 |
| (NH$_4$)$_2$O, wt % | 5.75 | 5.37 |
| K$_2$O, wt % | 3.22 | 3.09 |
| Fe$_2$O$_3$, wt % | 0.99 | — |
| TiO$_2$, wt % | — | 1.14 |
| Al$_2$O$_3$, wt % | 16.80 | 16.00 |
| SiO$_2$, wt % | 68.93 | 70.63 |
| F$_2$, wt % | — | 0.08 |
| Na$^+$/Al | 0.03 | 0.02 |
| NH$_4{}^+$/Al | 0.67 | 0.66 |
| K$^+$/Al | 0.21 | 0.21 |
| Cation Equivalent, M$^+$/Al | 0.91 | 0.89 |
| SiO$_2$/Al$_2$O$_3$ | 6.96 | 7.49 |
| Si/(Al$_2$ + Ti$_2$) | 6.96 | 7.16 |

A comparison of the properties of the LZ-232 product with the starting erionite is shown in Table 18:

TABLE 18

| | Starting Erionite | LZ-232 Product |
|---|---|---|
| X-Ray Crystallinity: | | |
| % by Peak Instensity: | 100 | 172 |
| % by Peak Area: | 100 | 155 |
| Crystal Collapse Temp., °C. (DTA): | 975 | 985 |
| Framework Infrared: | | |
| Asymmetric Stretch, cm$^{-1}$: | 1052 | 1070 |
| Symmetric Stretch, cm$^{-1}$: | 781 | 782 |
| Hydroxyl Infrared: | | |
| Absolute Absorbance 3710 cm$^{-1}$: | 0.070 | 0.060 |
| Defect Structure Factor, z: | 0.030 | 0.026 |
| McBain Adsorption: | | |
| wt % O$_2$, 100 torr. −183° C.: | 17.75 | 18.58 |
| wt % H$_2$O, 4.6 torr, 25° C.: | 16.47 | 18.08 |

The framework mole fractions of tetrahedra are set forth below for the starting erionite and the LZ-232 product:

(a) Mole fractions of oxides (TO$_2$):
  Starting Erionite: (Al$_{0.217}$Si$_{0.753}$☐$_{0.030}$)O$_2$
  LZ-232 product: (Al$_{0.202}$Si$_{0.763}$Ti$_{0.009}$☐$_{0.026}$)O$_2$
(b) Mole fraction of aluminum removed, N: 0.015
(c) Percent aluminum removed, N/a×100: 7
(d) Change in Defect Structure Factor, Δz: −0.004
(e) Moles of titanium substituted per mole of aluminum removed: 0.60 (2) The molecular sieves denominated herein as "LZ-232" have the characteristic crystal structure of Zeolite Erionite as indicated by an x-ray powder diffraction pattern having at least the d-spacings set forth in Table J below and having titanium atoms in the crystal lattice in the form of TiO$_4$ tetrahedra, preferably in an amount of at least 1.0 per 10,000 Å$^3$:

TABLE J

| d,(Å) | Relative Intensity |
|---|---|
| 11.3 ± 0.5 | vs |
| 6.6 ± 0.2 | s |
| 4.33 ± 0.1 | m |
| 3.82 ± 0.1 | m |

TABLE J-continued

| d,(Å) | Relative Intensity |
|---|---|
| 3.76 ± 0.1 | m |
| 3.31 ± 0.1 | m |
| 2.86 ± 0.1 | m |
| 2.81 ± 0.1 | m |

EXAMPLE 10

(1) Twenty grams of an ammonium-exchanged synthetic zeolite W. containing 120.9 millimoles of aluminum, as $Al_2O_3$, were slurried in 500 ml distilled $H_2O$. Because of the limited solubility of $(NH_4)_2TiF_6$, the salt was added to the slurry as crystals. The weight of added $(NH_4)_2TiF_6$ was 12.40 grams and was an amount sufficient to replace 52% of the aluminum of the zeolite with titanium. The reaction mixture was then refluxed for 30 minutes, filtered and washed with warm distilled water until testing of the wash water was negative for both aluminum and fluoride ions.

The chemical analyses for the starting zeolite W and the molecular sieve product (referred to herein as LZ-230) are set forth in Table 19:

TABLE 19

|  | Starting $NH_4W$ | LZ-230 Product |
|---|---|---|
| $Na_2O$, wt % | 0.04 | 0.06 |
| $(NH_4)_2O$, wt % | 10.50 | 7.81 |
| $K_2O$, wt % | 0.08 | 0.09 |
| $TiO_2$, wt % | — | 16.09 |
| $Al_2O_3$, wt % | 30.82 | 16.69 |
| $SiO_2$, wt % | 67.29 | 58.93 |
| $F_2$, wt % | — | 0.14 |
| $Na^+/Al$ | 0.01 | 0.01 |
| $NH_4^+/Al$ | 0.68 | 0.92 |
| $K^+/Al$ | 0.01 | 0.01 |
| Cation Equivalent, $M^+/Al$ | 0.70 | 0.93 |
| $SiO_2/Al_2O_3$ | 3.71 | 5.99 |
| $Si/(Al_2 + Ti_2)$ | 3.71 | 3.71 |

A comparison of the properties of the LZ-230 product with the starting $NH_4W$ is shown in Table 20:

TABLE 20

|  | Starting $NH_4W$ | LZ-230 Product |
|---|---|---|
| X-Ray Crystallinity: |  |  |
| % by Peak Instensity: | 100 | 38 |
| % by Peak Area: | 100 | 38 |
| Crystal Collapse Temp.,° C. (DTA): | 1030 | 1010 |
| Framework Infrared: |  |  |
| Asymmetric Stretch, $cm^{-1}$: | 1023 | 1035 |
| Symmetric Stretch, $cm^{-1}$: | 783,761 | 784,761 |
| Hydroxyl Infrared: |  |  |
| Absolute Absorbance 3710 $cm^{-1}$: | 0.053 | 0.269 |
| Defect Structure Factor, z: | 0.023 | 0.114 |
| McBain Adsorption: |  |  |
| wt % $O_2$, 100 torr. −183° C.: | 0 | 5.21 |
| wt % $H_2O$, 4.6 torr. 25° C.: | 1.28 | 10.26 |

The framework mole fractions of tetrahedra are set forth below for the starting $NH_4W$ and the LZ-230 product..

(a) Mole fractions of oxides ($TO_2$):

Starting $NH_4W$ : $(Al_{0.343}Si_{0.634}\square_{0.023})O_2$
LZ-230 product: $(Al_{0.192}Si_{0.576}Ti_{0.118}\square_{0.114})O_2$ (b) Mole fraction of aluminum removed, N: 0.151
(c) Percent aluminum removed. $N/a \times 100$: 44
(d) Change in Defect Structure Factor, $\Delta z$: 0.091
(e) Moles of titanium substituted per mole of aluminum removed: 0.78

(2) The molecular sieves denominated herein as "LZ-230" have the characteristic crystal structure of Zeolite W as indicated by an x-ray powder diffraction pattern having at least the d-spacings set forth in Table K below and having titanium atoms in the crystals lattice in the form to $TiO_4$ tetrahedra, preferably in an amount of at least 1.0 per $10,000Å^3$.

TABLE K

| d(Å) | Relative Intensity |
|---|---|
| 8.2 ± 0.2 | ms |
| 7.1 ± 0.2 | vs |
| 5.3 ± 0.1 | ms |
| 5.0 ± 0.1 | ms |
| 4.5 ± 0.1 | mw |
| 4.31 ± 0.1 | mw |
| 3.67 ± 0.1 | m |
| 3.25 ± 0.1 | s |
| 3.17 ± 0.1 | s |
| 2.96 ± 0.1 | m |
| 2.73 ± 0.1 | m |
| 2.55 ± 0.1 | mw |

(3) The measured low X-ray crystallinity of the LZ-230 product shown in Table 20 is inconsistent with the measured increase in adsorption capacity for $O_2$ and $H_2O$. All properties taken together lead to the conclusion that the 16.09 wt. % $TiO_2$ found in the LZ-230 product represents titanium incorporated into the zeolite W framework.

EXAMPLE 11

Products of Examples 1, 2, 3, 4, 5 and 6 were tested for n-butane cracking activity and found to be active catalysts. The results of those tests are shown in Tables 21, 22 and 23.

TABLE 21

| Product | Example | Consumption of n-Butane | $k_a$* |
|---|---|---|---|
| $NH_4Y$ | — | 11.1 | 1.9 |
| $NH_4Y$ | — | 29.5 | 4.3 |
| LZ-224 | 2 | 14.0 | 6.4 |
| LZ-225 | 1 | 2.0 | 3.9 |

*The lower the value for $k_a$ the lower activity.

TABLE 22

| Product | Example | Consumption of n-Butane | $k_a$* |
|---|---|---|---|
| $NH_4$ Mordenite | — | 77.3 | 177 |
| LZ-226 | 4 | 13.3 | 5.2 |
| LZ-227 | 3 | 60.8 | 44.7 |

*The lower the value for $k_a$ the lower the activity.

TABLE 23

| Product | Example | Consumption of n-Butane | $k_a$* |
|---|---|---|---|
| $NH_4,L$ | — | 26.0 | 5.0 |
| LZ-228 | 6 | 12.9 | 4.8 |
| LZ-229 | 5 | 6.5 | 4.2 |

*The lower the value for $k_a$ the lower the activity.

EXAMPLE 12

(1) Five grams of an ammonium-exchanged ZSM-5 zeolite containing 5.10 millimoles of aluminum, as $Al_2O_3$, were slurried in 100 ml distilled $H_2O$. Because of the limited solubility of $(NH_4)_2TiF_6$, the salt was added to the slurry as crystals. The weight of added $(NH_4)_2TiF_6$ was 1.00 gm and was an amount sufficient to replace 100% of the aluminum of the zeolite with titanium. The ZSM-5 zeolite and $(NH_4)_2TiF_6$ slurry were refluxed for 52 hours, filtered and washed with warm distilled water until qualitative tests of the wash water were negative for both aluminum and fluoride ions. The chemical analyses for the starting $NH_4$-ZSM-5 and the molecular sieve product (referred to herein as LZ-241) are set forth in Table 24.

TABLE 24

|  | Starting $NH_4$—ZSM-5 | LZ-241 Product |
|---|---|---|
| $Na_2O$, wt %: | 0.08 | N.D.* |
| $(NH_4)_2O$, wt %: | 1.95 | 1.18 |
| $TiO_2$, wt %: | — | 8.88 |
| $Al_2O_3$, wt %: | 5.09 | 2.60 |
| $SiO_2$, wt %: | 93.07 | 88.34 |
| $F_2$, wt %: | 0 | <0.1 |
| $Na^+/Al$: | 0.03 | 0.0 |
| $NH_4^+/Al$: | 0.75 | 0.89 |
| Cation Equivalent $M^+/Al$: | 0.78 | 0.89 |
| $SiO_2/Al_2O_3$: | 31.04 | 57.65 |
| $Si/(Al_2 + Ti_2)$: | — | 18.15 |

*none detected

A comparison of the properties of the LZ-241 product with the starting $NH_4^-$-ZSM-5 is shown in Table 25.

TABLE 25

|  | Starting $NH_4$—ZSM-5 | LZ-241 Product |
|---|---|---|
| X-Ray Crystallinity | | |
| % by Peak Intensity: | 100 | 80 |
| % by Peak Area: | 100 | 72 |
| Framework Infrared: | | |
| Asymmetric Stretch $cm^{-1}$: | 1098 | 1103 |
| Symmetric Stretch $cm^{-1}$: | 794 | 797 |
| Hydroxyl Infrared | | |
| Absolute Absorbance | | |
| 3710 $cm^1$: | 0.195 | 0.145 |
| Defect Structure | | |
| Fractor, Z: | 0.082 | 0.062 |

(2) The novel zeolites denominated LZ-241 have the characteristic crystal structure of zeolite ZSM-5 as indicated by an X-ray diffraction pattern having at least the d-spacings set forth in Table M below and having extraneous titanium atoms in the crystal lattice in the form of $TiO_4$ tetrahedra, preferable in an amount of at least 1.0 per 10,000Å$^3$.

TABLE M

| d(Å) | Relative Intensity |
|---|---|
| 11.1 ± 0.2 | very strong |
| 10.0 ± 0.2 | strong |
| 6.3 ± 0.1 | weak |
| 6.0 ± 0.1 | weak |
| 5.56 ± 0.1 | medium weak |
| 5.01 ± 0.1 | weak |
| 4.60 ± 0.1 | weak |
| 4.25 ± 0.1 | weak |
| 3.85 ± 0.1 | strong |
| 3.71 ± 0.1 | medium |
| 3.0 ± 0.1 | medium |

TABLE M-continued

| d(Å) | Relative Intensity |
|---|---|
| 2.99 ± 0.1 | medium weak |

Figure 2:
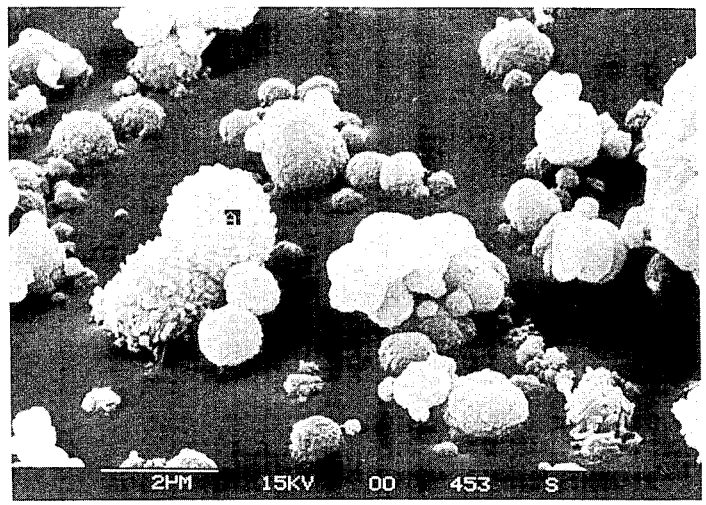
FIGS. 2 and 3 are SEM (Scanning Electron Micrographs) of ZSM-5 and LZ-241, respectively, as hereinafter discussed.
Figure 3:
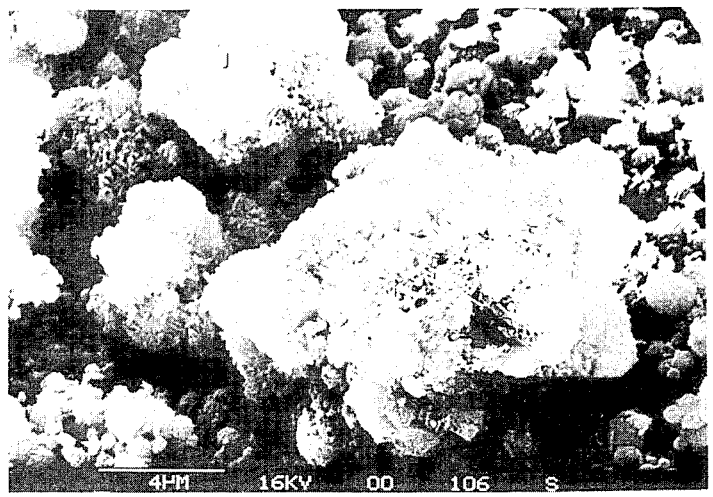
Figure 4:
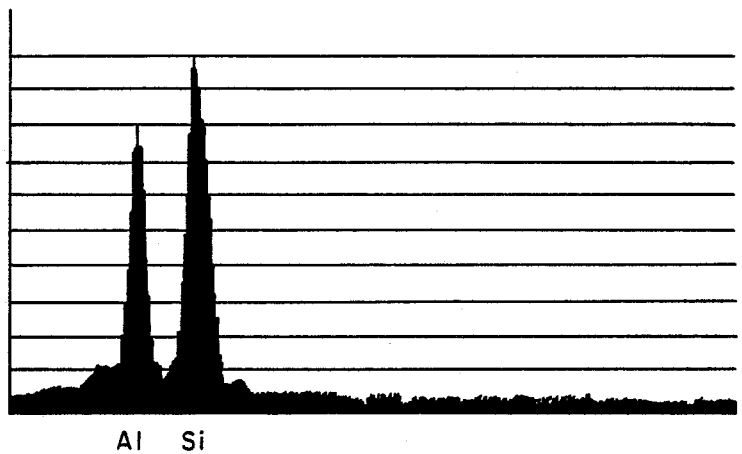
FIGS. 4 and 5 are EDAX (Energy Disperive Analysis by X-ray) graphs for ZSM-5 and LZ-241, respectively, as hereinafter discussed.
Figure 5:
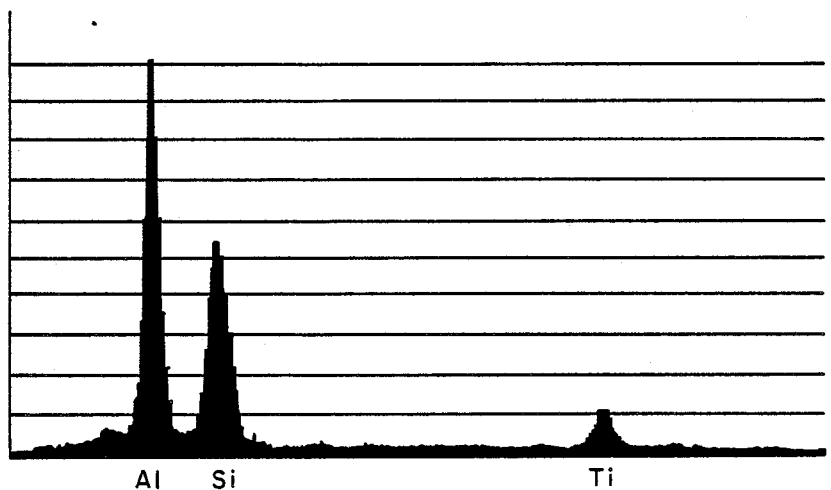

(3) To demonstrate that the titanium in the LZ-241 Product is associated with the ZSM-5 crystals. Scanning Electron Micrographs (SEM) for the starting ZSM-5 and the LZ-241 product were obtained and are shown in FIGS. 2 and 3, respectively. The EDAX identification of the elements found in the samples at the designated locations on the respective zeolite crystals for ZSM-5 and LZ-241, respectively, are shown in FIGS. 4 and 5. Quite clearly, titanium is located in the crystals of the LZ-241 product. The properties of LZ-241 are consistent with the conclusion that the 8.88 wt. percent $TiO_2$ found in the LZ-241 product represents titanium incorporated into the framework of the ZSM-5 zeolite.

EXAMPLE 13

This is a comparative example wherein example 1 of European patent application No. 82109451.3 was repeated and the product evaluated by several techniques as hereinafter discussed:

(a) Example 1 of European patent application No. 82109451.3 was repeated with the starting reaction mixture having a composition based on molar ratios of:

1 $Al_2O_3$:47 $SiO_2$:1.32 $TiO_2$:11.7 NaOH;28 TPAOH:1498 $H_2O$

The reaction mixture was divided and placed in two digestion vessels. At the end of the procedure set forth in example 1 of the European Application a sample of the product from each digestion vessel was analyzed and gave the following chemical analyses:

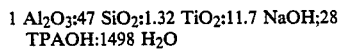

|  | Weight Percent | |
|---|---|---|
|  | Sample 1 | Sample 2 |
| $SiO_2$ | 75.3 | 75.9 |
| $Al_2O_3$ | 3.02 | 2.58 |
| $TiO_2$ | 3.91 | 4.16 |
| $Na_2O$ | 3.66 | 3.46 |
| Carbon | 6.3 | 6.7 |
| Nitrogen | 0.62 | 0.65 |
| LOI* | 14.0 | 14.0 |

*Loss on Ignition

Figure 6:
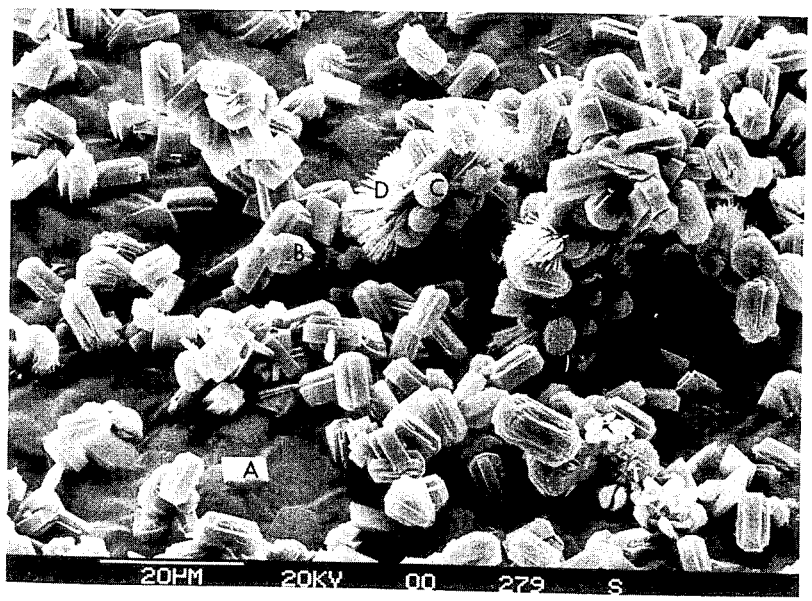
FIG. 6 is a Scanning Electron Micrograph of a product prepared in accordance to European patent application Ser. No. 82109451.3, as hereinafter discussed.

The two samples were then analyzed by SEM (scanning electron microscope) and EDAX (energy dispersive analysis by x-ray) microprobe. The SEM probe of the two samples showed four morphologies to be present and such are shown in FIG. 6. The four morphologies of the two samples prepared in accordance with the European application and the EDAX microprobe analysis for each morphology was as follows:

(1) Smooth, intergrown hexagonal particles (at B in FIG. 6) which are associated with a ZSM-5 morphology had an EDAX microprobe of:

|  | Average of Spot Probes |
|---|---|
| Ti | 0 |
| Si | 1.0 |
| Al | 0.05 |

(2) Flat, smooth plates (at A in FIG. 6) had an EDAX microprobe of:

| | Average of Spot Probes |
|---|---|
| Ti | 0.13 |
| Si | 1.0 |
| Al | 0.05 |

(3) Spheres and elongated bundles (at C in FIG. 6) had an EDAX microprobe of:

| | Average of Spot Probes |
|---|---|
| Ti | 0.22 |
| Si | 1.0 |
| Al | 0.05 |
| Na | 0.10 |

(4) Needles or fine rods (at D in FIG. 6) had an EDAX microprobe of:

| | Average of Spot Probes |
|---|---|
| Ti | 0.05 |
| Si | 0.8 |
| Al | 0.13 |
| Na | 0.05 |
| Cl | 0.10 |

The above SEM and EDAX data demonstrate that although ZSM-5 type crystals were formed that these crystals contained no detectable titanium. The only detectable titanium was present as impurity phases and was not present in a crystal having the ZSM-5 structure.

The X-ray diffraction patterns of the as-synthesized materials were obtained and the following X-ray patterns were observed:

TABLE X

| (Sample 1) | |
|---|---|
| $2\Theta$ | d(A) |
| 5.577 | 15.8467 |
| 5.950 | 14.8540 |
| 6.041 | 14.6293 |
| 6.535 | 13.5251 |
| 7.154 | 12.3567 |
| 7.895 | 11.1978 |
| 8.798 | 10.0504 |
| 9.028 | 9.7946 |
| 9.784 | 9.0401 |
| 11.846 | 7.4708 |
| 12.453 | 7.1079 |
| 12.725 | 6.9565 |
| 13.161 | 6.7267 |
| 13.875 | 6.3821 |
| 14.637 | 6.0518 |
| 14.710 | 6.0219 |
| 15.461 | 5.7310 |
| 15.881 | 5.5802 |
| 16.471 | 5.3818 |
| 17.218 | 5.1498 |
| 17.695 | 5.0120 |
| 19.212 | 4.6198 |
| 19.898 | 4.4619 |
| 20.045 | 4.4295 |
| 20.288 | 4.3770 |
| 20.806 | 4.2692 |
| 21.681 | 4.0988 |
| 22.143 | 4.0145 |
| 23.091 | 3.8516 |
| 23.641 | 3.7632 |
| 23.879 | 3.7263 |
| 24.346 | 3.6559 |
| 24.649 | 3.6116 |
| 25.548 | 3.4865 |
| 25.828 | 3.4494 |
| 26.228 | 3.3976 |
| 26.608 | 3.3501 |
| 26.887 | 3.3158 |
| 27.422 | 3.2524 |
| 28.048 | 3.1812 |
| 28.356 | 3.1473 |
| 29.191 | 3.0592 |
| 29.912 | 2.9870 |
| 30.295 | 2.9502 |
| 32.736 | 2.7356 |
| 33.362 | 2.6857 |
| 34.355 | 2.6102 |
| 34.640 | 2.5894 |
| 34.887 | 2.5716 |
| 35.152 | 2.5529 |
| 35.551 | 2.5252 |
| 35.660 | 2.5177 |
| 36.031 | 2.4926 |
| 37.193 | 2.4174 |
| 37.493 | 2.3987 |
| 45.066 | 2.0116 |
| 45.378 | 1.9985 |
| 46.514 | 1.9523 |
| 47.393 | 1.9182 |

TABLE XI

| (Sample 2) | |
|---|---|
| $2\Theta$ | d(A) |
| 5.801 | 15.2353 |
| 6.012 | 14.7012 |
| 6.169 | 14.3265 |
| 7.970 | 11.0926 |
| 8.875 | 9.9636 |
| 9.118 | 9.6981 |
| 9.879 | 8.9532 |
| 11.933 | 7.4163 |
| 12.537 | 7.0605 |
| 12.808 | 6.9115 |
| 13.242 | 6.6860 |
| 13.957 | 6.3452 |
| 14.718 | 6.0186 |
| 14.810 | 5.9813 |
| 15.542 | 5.7014 |
| 15.954 | 5.5551 |
| 16.563 | 5.3521 |
| 17.316 | 5.1211 |
| 17.788 | 4.9862 |
| 19.291 | 4.6009 |
| 20.119 | 4.4134 |
| 20.382 | 4.3571 |
| 20.879 | 4.2544 |
| 21.735 | 4.0887 |
| 22.220 | 4.0007 |
| 23.170 | 3.8387 |
| 23.730 | 3.7494 |
| 23.964 | 3.7133 |
| 24.425 | 3.6442 |
| 24.722 | 3.6011 |
| 25.900 | 3.4399 |
| 26.734 | 3.3345 |
| 26.979 | 3.3047 |
| 27.251 | 3.2724 |
| 27.494 | 3.2440 |
| 28.175 | 3.1671 |
| 28.450 | 3.1371 |
| 29.287 | 3.0493 |
| 29.970 | 2.9814 |
| 30.371 | 2.9430 |
| 30.694 | 2.9127 |
| 31.312 | 2.8566 |
| 32.825 | 2.7283 |
| 33.457 | 2.6782 |
| 34.426 | 2.6051 |
| 34.723 | 2.5834 |
| 34.879 | 2.5722 |

TABLE XI-continued (Sample 2)

| 2Θ | d(A) |
|---|---|
| 35.709 | 2.5143 |
| 36.125 | 2.4863 |
| 37.248 | 2.4139 |
| 37.490 | 2.3988 |
| 45.156 | 2.0078 |
| 45.453 | 1.9954 |
| 46.462 | 1.9544 |
| 46.608 | 1.9486 |

Tables X and XI shows an X-ray pattern typical of a ZSM-5 type product and can be attributed to the smooth, integrown hexagonal particles which contained no titanium. The X-ray patterns of Tables X and XI show three peaks (2Θ =5.6–5.8, 12.45–12.54 and 24.5–14.72) which could not be explained. Two samples were calcined with a separate portion of each sample being calcined in air 540° C. for sixteen hours. These calcination conditions correspond to those employed in European Application No. 82109451.3. The X-ray patterns of the calcined products were as follows:

TABLE XII (Sample 1)

| 2Θ | d(A) |
|---|---|
| 6.141 | 14.3908 |
| 6.255 | 14.1303 |
| 8.011 | 11.0355 |
| 8.913 | 9.9209 |
| 9.144 | 9.6705 |
| 9.930 | 8.9068 |
| 11.979 | 7.3876 |
| 12.440 | 7.1152 |
| 13.289 | 6.6625 |
| 14.007 | 6.3224 |
| 14.874 | 5.9557 |
| 15.613 | 5.6757 |
| 15.995 | 5.5408 |
| 16.609 | 5.3373 |
| 17.353 | 5.1103 |
| 17.884 | 4.9597 |
| 19.335 | 4.5905 |
| 20.177 | 4.4008 |
| 20.463 | 4.3401 |
| 20.940 | 4.2422 |
| 21.845 | 4.0685 |
| 22.291 | 3.9880 |
| 23.186 | 3.8361 |
| 23.362 | 3.8076 |
| 23.817 | 3.7359 |
| 24.031 | 3.7031 |
| 24.510 | 3.6317 |
| 24.908 | 3.5747 |
| 25.699 | 3.4664 |
| 25.969 | 3.4309 |
| 26.371 | 3.3796 |
| 26.698 | 3.3389 |
| 27.022 | 3.2996 |
| 27.487 | 3.2449 |
| 28.184 | 3.1662 |
| 28.513 | 3.1303 |
| 29.369 | 3.0411 |
| 30.017 | 2.9769 |
| 30.468 | 2.9338 |
| 31.333 | 2.8548 |
| 32.877 | 2.7241 |
| 34.490 | 2.6003 |
| 35.062 | 2.5592 |
| 35.800 | 2.5082 |
| 36.186 | 2.4823 |
| 37.324 | 2.4092 |
| 37.654 | 2.3888 |
| 45.195 | 2.0062 |
| 45.631 | 1.9880 |
| 46.639 | 1.9474 |
| 47.547 | 1.9123 |

TABLE XII-continued (Sample 1)

| 2Θ | d(A) |
|---|---|
| 48.765 | 1.8674 |

TABLE III (Sample 2)

| 2θ | d(A) |
|---|---|
| 6.092 | 14.5084 |
| 6.295 | 14.0403 |
| 7.941 | 11.1328 |
| 8.838 | 10.0054 |
| 9.857 | 8.9730 |
| 11.921 | 7.4236 |
| 12.399 | 7.1383 |
| 13.222 | 6.6959 |
| 13.937 | 6.3539 |
| 14.811 | 5.9809 |
| 15.535 | 5.7038 |
| 15.916 | 5.5681 |
| 16.532 | 5.3620 |
| 17.262 | 5.1370 |
| 17.806 | 4.9811 |
| 19.268 | 4.6064 |
| 20.107 | 4.4160 |
| 20.389 | 4.3556 |
| 20.868 | 4.2567 |
| 21.807 | 4.0754 |
| 22.197 | 4.0047 |
| 23.116 | 3.8476 |
| 23.263 | 3.8235 |
| 23.755 | 3.7455 |
| 23.955 | 3.7147 |
| 24.432 | 3.6433 |
| 24.854 | 3.5823 |
| 25.653 | 3.4725 |
| 25.901 | 3.4398 |
| 26.265 | 3.3929 |
| 26.648 | 3.3451 |
| 26.976 | 3.3052 |
| 27.386 | 3.2566 |
| 28.156 | 3.1692 |
| 28.495 | 3.1323 |
| 29.304 | 3.0476 |
| 29.969 | 2.9815 |
| 30.384 | 2.9417 |
| 31.283 | 2.8592 |
| 32.819 | 2.7289 |
| 34.423 | 2.6052 |
| 34.993 | 2.5641 |
| 35.716 | 2.5138 |
| 36.146 | 2.4850 |
| 37.295 | 2.4110 |
| 37.562 | 2.3944 |
| 45.137 | 2.0086 |
| 45.523 | 1.9925 |
| 46.562 | 1.9504 |
| 47.509 | 1.9137 |

The X-ray diffraction patterns of the calcined samples show a ZSM-5 type pattern with only slight differences from the as-synthesized. When chemical analysis (bulk) of a portion of the calcined samples 1 and 2 are carried out the following is obtained:

| | Weight Percent | |
|---|---|---|
| | Sample 1 | Sample 2 |
| $SiO_2$ | 79.6 | 81.2 |
| $Al_2O_3$ | 3.5 | 2.9 |
| $Na_2O$ | 4.4 | 4.1 |
| $TiO_2$ | 4.4 | 4.6 |
| C | 0.1 | 0.10 |
| LOI | 8.1 | 7.6 |

When the molar ratio of oxides is computed for the above bulk analysis the following is obtained:

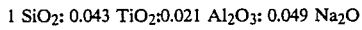

This compares quite well with the bulk chemical analysis reported in the European application which is:

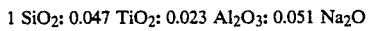

Although it is clear that the product crystals which gave the product an X-ray pattern characteristic of ZSM-5 contained no titanium, the bulk analysis of the product showed titanium to be present as a result of impurity crystal not having an X-ray pattern characteristic of ZSM-5.

PROCESS APPLICATIONS

The molecular sieves compositions of this invention have unique surface characteristics making them useful as molecular sieves and as catalyst or as bases for catalysts in a variety of separation, hydrocarbon conversion and oxidative combustion processes. These composition can be impregnated or otherwise associated with catalytically active metals by the numerous methods know in the art and used, for example, in fabricating catalysts compositions containing alumina or aluminosilicate materials.

The instant molecular sieve compositions may be employed for separating molecular species in admixture with molecular species of a different degree of polarity or having different kinetic diameters by contacting such mixtures with a molecular sieve composition having pore diameters large enough to adsorb at least one but not all molecular species of the mixture based on the polarity of the adsorbed molecular species and/or its kinetic diameter. When the instant compositions are employed for such separation processes the compositions are at least partially activated whereby some molecular species selectively enter the intracrystalline pore system thereof.

The hydrocarbon conversion reactions which may be catalyzed by the instant molecular sieve compositions include; cracking, hydrocracking; alkylation of both the aromatic and isoparaffin types; isomerization (including xylene isomerization); polymerization; reforming; hydrogenation; dehydrogenation; transalkylation; dealkylation; and hydration.

When catalyst composition containing the instant molecular sieve compositions also contains a hydrogenation promoter, such promoter may be platinum, palladium, tungsten, nickel or molybdenum and may be used to treat various petroleum stocks including heavy petroleum residual stocks, cyclic stocks and other hydrocrackable charge stocks. These stocks can be hydrocracked at temperatures in the range of between about 400° F. and about 825° F. using molar ratios of hydrogen to hydrocarbon in the range of between about 2 and about 80, pressures between about 10 and about 3500 p.s.i.g., and a liquid hourly space velocity (LHSV) of between about 0.1 and about 20, preferably between about 1.0 and about 10.

Catalyst compositions containing the instant molecular sieve compositions may also be employed in reforming processes in which the hydrocarbon feedstocks contact the catalyst at temperatures between about 700° F. and about 1000° F., hydrogen pressures of between about 100 and about 500 p.s.i.g., LHSV values in the range between about 0.1 and about 10 and hydrogen to hydrocarbon molar ratios in the range between about 1 and about 20, preferably between about 4 and about 12.

Further, catalysts containing the instant molecular sieve compositions which also contain hydrogenation promoters, are also useful in hydroisomerization processes wherein the feedstock(s), such as normal paraffins, is converted to saturated branched-chain isomers. Hydroisomerization processes are typically carried out at a temperature between about 200° F. and about 600° F., preferably between about 300° F. and about 550° F. with an LHSV value between about 0.2 and about 1.0. Hydrogen is typically supplied to the reactor in admixture with the hydrocarbon feedstock in molar proportions of hydrogen to the feedstock of between about 1 and about 5.

Catalyst compositions similar to those employed for hydrocracking and hydroisomerization may also be employed at between abut 650° F. and about 1000° F., preferably between about 850° F. and about 950° F. and usually at somewhat lower pressures within the range between about 15 and about 50 p.s.i.g. for the hydroisomerization of normal paraffins. Preferably the paraffin feedstock comprises normal paraffins having a carbon number range of $c_7-C_{20}$. The contact time between the feedstock and the TiSO containing catalyst is generally relatively short to avoid undersirable side reactions such as olefin polymerization and paraffin cracking. LHSV values in the range between about 0.1 and about 10, preferably between about 1.0 and about 6.0 are suitable.

The low alkali metal content (often not measurable by current analytical techniques) of the instant of the instant compositions make them particularly well suited for use in the conversion of alkylaromatic compounds, particularly for use in the catalytic disproportionation of toluene, xylene, trimethylbenzenes, tetramethylbenzenes and the like. In such disproportionation processes it has been observed that isomerization and transalkylation can also occur. The catalysts containing the instant molecular sieve compositions and employed for such processes will typically include Group VIII noble metal adjuvants alone or in conjunction with Group VI-B metals such as tungsten, molybdenum and chromium which are preferably included in such catalyst compositions in amounts between about 3 and about 15 weight-% of the overall catalyst composition. Extraneous hydrogen can, but need not be present in the reaction zone which is maintained at a temperature between about 400° and about 750° F., pressures in the range between about 100 and about 2000 p.s.i.g. and LHSV values in the range between about 0.1 and about 15.

Catalysts containing the instant molecular sieve compositions may be employed in catalytic cracking processes wherein such are preferably employed with feedstocks such as gas oils, heavy naphthas, deasphalted crude oil residues etc. with gasoline being the principal desired product. Temperature conditions are typically between about 850° and about 1100° F., LHSV values between about 0.5 and about 10 pressure conditions are between about 0 p.s.i.g. and about 50 p.s.i.g.

Catalysts containing the instant molecular sieve compositions may be employed for dehydrocyclization reactions which employ paraffinic hydrocarbon feedstocks, preferably normal paraffins having more than 6 carbon atoms, to form benzene, xylenes, toluene and the like. Dehydrocyclization processes are typically carried out using reaction conditions similar to those employed for catalytic cracking. For such processes it is preferred to use a Group VIII non-noble metal cation such as cobalt and nickel in conjunction with the molecular sieve composition.

Catalysts containing the instant molecular sieve compositions may be employed in catalytic dealkylation where paraffinic side chains are cleaved from aromatic nuclei without substantially hydrogenating the ring structure at relatively high temperatures in the range between about 800° F. and about 1000° F. at moderate hydrogen pressures between about 300 and about 1000 p.s.i.g. with other conditions being similar to those described above for catalytic hydrocracking. Catalysts employed for catalytic dealkylation are of the same type described above in connection with catalytic dehydrocyclization. Particularly desirable dealkylation reactions contemplated herein include the conversion of methylnaphthalene to naphthalene and toluene and/or xylenes to benzene.

Catalysts containing the instant molecular sieve compositions may be used in catalytic hydrofining wherein the primary objective is to provide for the selective hydrodecomposition of organic sulfur and/or nitrogen compounds without substantially affecting hydrocarbon molecules present therewith. For this purpose it is preferred to employ the same general conditions described above for catalytic hydrocracking. The catalysts are the same typically of the same general nature as described in connection with dehydrocylization operations. Feedstocks commonly employed for catalytic hydroforming include: gasoline fractions; kerosenes; jet fuel fractions; diesel fractions; light and heavy gas oils; deasphalted crude oil residua; and the like. The feedstock may contain up to about 5 weight-percent of sulfur and up to about 3 weight-percent of nitrogen.

Catalysts containing the instant molecular sieve compositions may be employed for isomerization processes under conditions similar to those described above for reforming although isomerization processes tend to require somewhat more acidic catalysts than those employed in reforming processes. Olefins are preferably isomerized at temperatures between about 500° F. and about 900° F., while paraffins, naphthenes and alkyl aromatics are isomerized at temperatures between about 700° F. and about 1000° F. Particularly desirable isomerization reactions contemplated herein include the conversion of n-heptane and/or n-octane to isoheptanes, iso-octanes, butane to iso-butane, methylcyclopentane to cylcohexane, meta-xylene and/or ortho-xylene to para-xylene, 1-butene to 2-butene and/or iso-butene, n-hexene to isohexane, cyclohexane to methylcyclopentene etc. The preferred cation form is a combination of a molecular sieve of this invention and polyvalent metal compounds (such as sulfides) of metals of Group II-A, Group II-B and rare earth metals. For alkylation and dealkylation processes the instant molecular sieve compositions having pores of at least 5Å are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450' F. and not greater than the critical temperature of the compound undergoing dealkylation. Pressure conditions are applied to retain at least the aromatic feed in the liquid state. For alkylation the temperature can be as low as 250° F. but is preferably at least 350° F. In alkylation of benzene, toluene and xylene, the preferred alkylation agents are olefins such as ethylene and propylene.

The molecular sieve compositions of this invention may be employed in conventional molecular sieving processes as heretofore have been carried out using aluminosilicate, aluminophosphate or other commonly employed molecular sieves. The instant compositions are preferably activated, e.g. calcined in air or nitrogen, prior to their use in a molecular sieve process.

The molecular sieve compositions of this invention are also useful as adsorbents and are capable of separating mixtures of molecular species both on the basis of molecular size (kinetic diameters) and based on the degree of polarity of the molecular species. When the separation of molecular species is based upon selective adsorption based on molecular size, the instant molecular sieve composition is chosen in view of the dimensions of its pores such that at least the smallest molecular specie of the mixture can enter the intracrystalline void space while at least the largest specie is excluded. When the separation is based on degree of polarity it is generally the case that the more hydrophilic molecular sieve composition will preferentially adsorb the more polar molecular species of a mixture having different degrees of polarity even though both molecular species can communicate with the pore system of the molecular sieve composition.

What is claimed is:

1. The process for preparing molecular sieves containing at least one of titanium and/or iron from a starting crystalline aluminosilicate which comprises contacting said crystalline aluminosilicate having pore diameters of at least about 3 Angstroms and having a molar $SiO_2/Al_2O_3$ ratio of at least 3, with a fluoro salt of titanium and/or iron, said fluoro salt being in the form of a solution or slurry, whereby framework aluminum atoms of the starting crystalline aluminosilicate are removed and replaced by at least one of titanium and iron.

2. Method according to claim 1 wherein the starting crystalline aluminosilicate is at least partially in the ammonium cationic form.

3. Method according to claim 2 wherein the fluoro salt is a titanium fluoro salt.

4. Method according to claim 1 wherein said fluoro salt is in the form of an aqueous solution or slurry.

5. Method according to claim 1 wherein the starting crystalline aluminosilicate is selected from the group consisting of zeolite Y and ZSM-5 and the fluoro salt is a fluoro salt of titanium.

6. Method according to claim 1 wherein the starting crystalline aluminosilicate has the essential crystal structure of zeolite Y.

7. Method according to claim 1 wherein the starting crystalline aluminosilicate has the essential crystal structure of mordenite.

8. Method according to claim 1 wherein the starting crystalline aluminosilicate has the essential crystal structure of zeolite L.

9. Method according to claim 1 wherein the starting crystalline aluminosilicate has the essential crystal structure of zeolite W.

10. Method according to claim 1 wherein the starting crystalline aluminosilicate has the essential crystal structure of TMA offretite.

11. Method according to claim 1 wherein the starting crystalline aluminosilicate has the essential crystal structure of clinoptilolite.

12. Method according to claim 1 wherein the starting crystalline aluminosilicate has the essential crystal structure of erionite.

13. Method according to claim 1 wherein the starting crystalline aluminosilicate has the essential crystal structure of ZSM-5.

14. Method according to claim 2 wherein the fluoro salt is an iron fluoro salt.

* * * * *